(12) United States Patent
Takamori

(10) Patent No.: US 9,904,992 B2
(45) Date of Patent: Feb. 27, 2018

(54) PACKETED DRUG INSPECTION DEVICE AND METHOD

(71) Applicant: FUJIFILM Corporation, Tokyo (JP)

(72) Inventor: Tetsuya Takamori, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 72 days.

(21) Appl. No.: 14/973,849

(22) Filed: Dec. 18, 2015

(65) Prior Publication Data

US 2016/0104277 A1   Apr. 14, 2016

Related U.S. Application Data

(63) Continuation of application No. PCT/JP2014/065055, filed on Jun. 6, 2014.

(30) Foreign Application Priority Data

Jun. 21, 2013   (JP) ................. 2013-130725

(51) Int. Cl.
*G06T 7/00* (2017.01)
*G01J 3/46* (2006.01)
(Continued)

(52) U.S. Cl.
CPC .............. *G06T 7/0004* (2013.01); *G01J 3/46* (2013.01); *G01N 21/251* (2013.01);
(Continued)

(58) Field of Classification Search
CPC ......... B65B 5/103; B65B 57/10; B65B 57/20; G07F 17/0092; G07F 9/026; G07F 11/62;
(Continued)

(56) References Cited

U.S. PATENT DOCUMENTS 6,535,637 B1   3/2003   Wootton et al.
7,028,723 B1 *  4/2006   Alouani ................. B65B 5/101
                                                        141/83
(Continued)

FOREIGN PATENT DOCUMENTS

EP   2502611 A1   9/2012
JP   5-337168 A   12/1993
(Continued)

OTHER PUBLICATIONS

Communication dated Jun. 1, 2016 from the European Patent Office in counterpart application No. 14813472.9.
(Continued)

*Primary Examiner* — Kenny Cese
(74) *Attorney, Agent, or Firm* — Sughrue Mion, PLLC

(57) ABSTRACT

It is determined whether the type of drug inserted into a packaging machine is correct, on the basis of the dispensing information of the drug to be packaged and the drug type information of the drug to be inserted into the packaging machine. Number-by-appearance information indicating the number of drugs for each outward appearance which are packaged in each packet is acquired. The image of each drug corresponding to each dose is captured. The number of drugs for each outward appearance which are packaged in each packet is counted on the basis of the captured image of the drugs. It is determined whether the number of drugs for each outward appearance is correct, on the basis of the number-by-appearance information and the counting result of the number-by-appearance counting unit. It is determined whether the occurrence or non-occurrence of a mix-up of the drugs can be determined, on the basis of at least the dispensing information of the drugs to be packaged and the drug type information of the drugs inserted into the pack-
(Continued)

aging machine. It is determined whether the drugs packaged in each packet are correct.

18 Claims, 14 Drawing Sheets

(51) Int. Cl.
*G01N 21/25* (2006.01)
*G06K 9/46* (2006.01)
*G06K 9/62* (2006.01)
*B65B 57/10* (2006.01)
*B65B 5/10* (2006.01)
*G01N 21/95* (2006.01)

(52) U.S. Cl.
CPC ......... *G06K 9/4652* (2013.01); *G06K 9/6215* (2013.01); *B65B 5/103* (2013.01); *B65B 57/10* (2013.01); *G01N 21/9508* (2013.01); *G06T 2207/10024* (2013.01)

(58) Field of Classification Search
CPC ....... G07F 7/06; G07F 11/00; G01N 21/9508; G01N 21/251; A61J 7/02; A61J 1/03; A61J 7/0076; G06F 19/3462; G06F 19/3456; G06F 19/326; G06T 7/0004; G01J 3/46; G06K 9/4652; G06K 9/6215
See application file for complete search history.

(56) References Cited

U.S. PATENT DOCUMENTS

| | | | |
|---|---|---|---|
| 8,271,128 B1* | 9/2012 | Schultz | G06F 19/3462 700/236 |
| 2003/0174326 A1* | 9/2003 | Rzasa | G01J 3/02 356/326 |
| 2005/0002552 A1* | 1/2005 | Dunn | G01N 15/1475 382/133 |
| 2006/0088196 A1* | 4/2006 | Popovich, Jr. | G06T 7/001 382/128 |
| 2010/0091285 A1* | 4/2010 | Newcomb | G01N 21/255 356/408 |
| 2012/0200596 A1* | 8/2012 | Gotou | B07C 5/38 345/625 |
| 2012/0216485 A1 | 8/2012 | Amano et al. | |
| 2013/0142406 A1* | 6/2013 | Lang | G06K 9/6293 382/128 |
| 2013/0342676 A1* | 12/2013 | Amano | H04N 7/18 348/86 |

FOREIGN PATENT DOCUMENTS

| | | |
|---|---|---|
| JP | 2002279068 A | 9/2002 |
| JP | 2003-517335 A | 5/2003 |
| JP | 2004-167158 A | 6/2004 |
| JP | 2006167145 A | 6/2006 |
| JP | 2008-18230 A | 1/2008 |
| JP | 2011-104077 A | 6/2011 |
| JP | 2012-245032 A | 12/2012 |
| JP | 2013-17745 A | 1/2013 |
| JP | 2013-55970 A | 3/2013 |
| WO | 2012/147907 A1 | 11/2012 |
| WO | 2013021543 A1 | 2/2013 |

OTHER PUBLICATIONS

International Search Report for PCT/JP2014/065055 dated Aug. 12, 2014.
Written Opinion for PCT/JP2014/065055 dated Aug. 12, 2014.

* cited by examiner

PACKETED DRUG INSPECTION DEVICE AND METHOD

CROSS-REFERENCE TO RELATED APPLICATIONS

The present application is a Continuation of PCT International Application No. PCT/JP2014/065055 filed on Jun. 6, 2014 claiming priority under 35 U.S.C § 119(a) to Japanese Patent Application No. 2013-130725 filed on Jun. 21, 2013. Each of the above applications is hereby expressly incorporated by reference, in their entirety, into the present application.

BACKGROUND OF THE INVENTION

1. Field of the Invention

The present invention relates to a packaged drug inspection device and method which inspects drugs packaged in a packet.

2. Description of the Related Art

In recent years, for example, in a hospital, when a plurality of types of drug that are taken at different times (for example, after breakfast, after lunch, and after dinner) are prescribed for a patient, one-dose packaging has generally been performed which packages a dose of a plurality of types of drugs (for example, pills and capsules) in one packet. The one-dose packaging is performed as follows: a pharmacist picks drugs according to the prescription and sets each dose of drugs on a tray (also referred to as a tablet case) of a packaging machine; and the packaging machine automatically packages the drugs in the tray in each packet. In the one-dose packaging, in some cases, the pharmacist manually performs the picking of the drugs or the setting of the drugs on the tray. Therefore, a different type of drug or a different number of drugs from those described in the prescription are likely to be erroneously packaged. In addition, in the case of an apparatus which automatically selects and sets drugs, the drugs are likely to be caught in the apparatus and a different type of drug or a different number of drugs from those described in the prescription are likely to be erroneously packaged.

An automatic pill packaging machine disclosed in JP1993-337168A (JP-H05-337168A) captures an image of drugs before the drugs are packaged in a packet and compares the drug type information of the drug obtained by analyzing the captured image with drug type information which is input in advance from an information processing apparatus or a terminal to inspect whether the drugs packaged in the packet are correct.

A drug inspection device disclosed in JP2008-18230A manually or automatically captures an image of each dose of drugs which are packaged in each packet, analyzes the captured image to calculate the length or area of the drugs, and calculates the concentration values of R, G, and B for each pixel. Then, the drug inspection device checks whether the packaged drugs are identical to the drugs described in the prescription, on the basis of the analysis result of the image and the results of the comparison between the reference image data items of the drugs.

A recognition and check system disclosed in JP2003-517335A captures an image of the content of a container having drugs therein and analyzes the captured image to extract the features of the drugs including the color, shape, size, and marking of the drugs. Then, the recognition and check system compares the extracted features with the features of the drugs which are stored in a database in advance to determine whether the drugs dispensed into the container are identical to the drugs described in the prescription.

A drug inspection support device disclosed in JP2013-017745A and JP2012-245032A captures the silhouette and color of drugs in a packet and compares the shape or color of the drugs obtained by analyzing each captured image with the shape or color of the drugs registered in a database to perform a preliminary inspection process of specifying the name of the drugs in the packet. Then, the drug inspection support device performs a secondary inspection process of specifying the name of a drug, which has not been specified by the preliminary inspection process, using optical spectrum analysis.

A packaged drug inspection system disclosed in JP2013-55970A captures an image of drugs in a packet and analyzes the captured image to determine whether the drugs packaged in the packet are the same as those described in a prescription. The packaged drug inspection system removes, for example, the overlap between the drugs before capturing the image of the drug. Therefore, it is possible to accurately capture the image of the drugs in the packet.

A drug dispensing device disclosed in JP2011-104077A vibrates drugs corresponding to a dose before packaging to remove the overlap between the drugs, captures the image of the drugs, analyzes the captured image to count the number of drugs corresponding to a dose, and compares the counting result with prescription information to inspect the dispensing of the drugs.

A drug recognition device disclosed in JP2004-167158A compares the image of a package of the drugs picked by a pharmacist with a plurality of reference images, which are stored in a storage unit in advance in order to recognize the names of the drugs, to recognize the names of the drugs. In addition, when there are two or more reference images similar to the captured image, the drug recognition device prompts the pharmacist to specify a drug name.

SUMMARY OF THE INVENTION

However, in the case in which the image of the drugs is captured as disclosed in JP1993-337168A (JP-H05-337168A), JP2008-18230A, and JP2003-517335A, when a mark or marking required to identify the type of drug (drug type) is on the back of the drug or when the drugs overlap each other, it is difficult to obtain an accurate image of the drugs and thus to perform accurate determination. In addition, when the image of the drugs in the packet or the container is captured as disclosed in JP2008-18230A and JP2003-517335A, in some cases, it is difficult to obtain an accurate image of the drugs due to the reflection of light from the surface of the packet or the drugs which stand up vertically in the packet.

The structures disclosed in JP2013-55970A and JP2011-104077A can be combined with the structures disclosed in JP1993-337168A (JP-H05-337168A), JP2008-18230A, and JP2003-517335A. In this case, costs increase, but it is possible to prevent the overlap between the drugs or the vertical rise of the drugs in the packet. However, when a plurality of types of drugs having the same or similar outward appearance are put in one packet, it is difficult to identify the drugs even though the captured image is analyzed. As a result, it is difficult to accurately determine the type or number of drugs and thus to accurately inspect whether the drugs packaged in the packet are correct. That is, even when various image process techniques, image analysis techniques, and image recognition techniques are used, it is difficult to accurately determine whether the packaged drug is correct. Therefore, the pharmacist needs to inspect the drugs in all of the packets. As a result, it is difficult to reduce the burden on the pharmacist to perform inspect dispensing (also referred to as drug inspection or inspection).

When the optical spectrum analysis structures disclosed in JP2013-017745A and JP2012-245032A are combined with the structures for preventing, for example, the overlap between the drugs disclosed in JP2013-55970A and JP2011-104077A, it is possible to accurately determine whether the drugs are correct. However, in this case, the inspection device needs to have both a function of preventing, for example, the overlap between the drugs and an optical spectrum analysis function, which results in a significant increase in the manufacturing cost of the inspection device.

According to the structure disclosed in JP2004-167158A, it is possible to determine whether the drugs are picked according to the prescription. However, even when the picked drugs are correct, there is a concern that mix-up of the drugs will occur when the drugs are extracted from a package, such as a sheet, and are then set on the tray of the packaging machine. Therefore, even when the structure disclosed in JP2004-167158A is combined with the structures disclosed in JP1993-337168A (JP-H05-337168A), JP2008-18230A, JP2003-517335A, JP2013-017745A, JP2012-245032A, JP2013-55970A, and JP2011-104077A, it is difficult to accurately determine whether the drugs packaged in the packet are correct. As a result, it is difficult to reduce the burden of the pharmacist to dispensing inspection.

An object of the invention is to provide a packaged drug inspection device and method which can accurately determine whether a packaged drug is correct at a low cost.

In order to achieve the object of the invention, according to an aspect of the invention, there is provided a packaged drug inspection device including: a dispensing information acquisition unit that acquires dispensing information of drugs packaged in a packet; an inserted drug type information acquisition unit that acquires drug type information of the drugs inserted into a packaging machine which packages the drugs in the packet; an inserted drug type error determination unit that determines whether the type of the drug inserted into the packaging machine is correct, on the basis of at least the dispensing information and the drug type information; a number-by-appearance information acquisition unit that acquires number-by-appearance information indicating the number of drugs for each outward appearance, which correspond to each dose and are packaged in each packet, on the basis of at least the dispensing information and the drug type information; an imaging unit that captures an image of the drugs corresponding to each dose; a number-by-appearance counting unit that counts the number of drugs for each outward appearance, which correspond to each dose, on the basis of the image of the drugs captured by the imaging unit; a number-by-appearance error determination unit that determines whether the number of drugs for each outward appearance, which correspond to each dose, is correct, on the basis of the number-by-appearance information and the counting result of the number-by-appearance counting unit; a mix-up determinability determination unit that determines whether the occurrence or non-occurrence of a mix-up in which a different type of drug is put in the packet, instead of the drug to be put in the packet, can be determined, on the basis of at least the dispensing information and the drug type information; and a packaging error determination unit that determines whether the drugs packaged in each packet are correct, on the basis of the determination result of the number-by-appearance error determination unit and the determination result of the mix-up determinability determination unit, and determines that the drugs are correct when the number-by-appearance error determination unit determines that the number of drugs is correct and the mix-up determinability determination unit determines that the occurrence or non-occurrence of the mix-up can be determined.

According to the invention, it is possible to accurately determine whether the drugs packaged in each packet are correct. Therefore, it is possible to appropriately omit or simplify the dispensing inspection of the pharmacist on the drug which has been determined to be correct. In addition, it is possible to form the packaged drug inspection device at a low cost.

Preferably, the packaged drug inspection device according to the above-mentioned aspect further includes a drug information database that stores the type of drug and the drug type information recorded on a package of the drug so as to be associated with each other. It is preferable that the inserted drug type information acquisition unit acquires the drug type information from the package and the inserted drug type error determination unit determines whether the drug type is correct, on the basis of the dispensing information and the drug type information, with reference to the drug information database. According to this structure, it is possible to determine whether the type of drug inserted into the packaging machine is correct, on the basis of the drug type information recorded on the package of the drug.

It is preferable that the inserted drug type information acquisition unit acquires at least one of characters, a barcode, and electronic identification information recorded on the package as the drug type information. According to this structure, it is possible to determine whether the type of drug inserted into the packaging machine is correct, on the basis of the characters or the barcode recorded on the drug package or the electronic identification information recorded on an RF tag.

It is preferable that the drug information database stores information indicating a correspondence relationship between an original drug and a generic drug. Preferably, when the drug corresponding to the drug type information has the same active ingredients as the drug designated by the dispensing information, the inserted drug type error determination unit determines that the drug type is correct. According to this structure, even when a drug having the same active ingredients, such as a generic drug, is used instead of the drug designated by the dispensing information, it is possible to determine whether the type of the drug inserted into the packaging machine is correct.

Preferably, the packaged drug inspection device according to the above-mentioned aspect further includes a first display unit that displays the drug type when the inserted drug type error determination unit determines that the drug type is incorrect. According to this structure, it is possible to warn that the type of the drug inserted into the packaging machine is incorrect.

Preferably, the packaged drug inspection device according to the above-mentioned aspect further includes a drug appearance database that stores the type of the drug and drug appearance information indicating the outward appearance of the drug so as to be associated with each other. It is preferable that the number-by-appearance information acquisition unit acquires the number-by-appearance information, on the basis of the dispensing information and the drug type information, with reference to the drug appearance database. According to this structure, since the drug appearance database is provided, it is possible to easily acquire the number-by-appearance information on the basis of the packaged drug information.

It is preferable that the mix-up determinability determination unit acquires the drug appearance information of the drug from the drug appearance database and determines that the occurrence or non-occurrence of the mix-up cannot be determined when different types of drugs having the same or similar outward appearance are included in the drugs to be packaged on the basis of the drug appearance information, the dispensing information, and the drug type information. According to this structure, it is possible to determine whether the occurrence or non-occurrence of the mix-up can be determined, on the basis of the drug appearance information.

Preferably, the packaged drug inspection device according to the above-mentioned aspect further includes a second display unit that, when the mix-up determinability determination unit determines that the occurrence or non-occurrence of the mix-up cannot be determined, displays the determination result of the mix-up determinability determination unit. According to this structure, it is possible to warn that the occurrence or non-occurrence of the mix-up of different types of drugs cannot be determined.

It is preferable that the second display unit displays the drug whose mix-up cannot be determined. According to this structure, it is possible to call the attention of the pharmacist who performs, for example, dispensing inspection to the drug whose mix-up cannot be determined.

It is preferable that the drug appearance information includes information indicating at least one of the size, type, and color of the drug and the number-by-appearance counting unit counts the number of drugs for each outward appearance for each item corresponding to the drug appearance information. According to this structure, it is possible to determine whether the number of drugs for each outward appearance, which correspond to each dose is correct, on the basis of the number-by-appearance information and the counting result of the number-by-appearance counting unit.

Preferably, the packaged drug inspection device according to the above-mentioned aspect further includes a third display unit that, when the number-by-appearance error determination unit determines that the number of drugs is incorrect, displays the determination result of the number-by-appearance error determination unit. According to this structure, it is possible to warn that the number of drugs for each outward appearance, which correspond to each dose, is incorrect.

It is preferable that the imaging unit captures the image of the drugs before the drugs are packaged in each packet and/or after the drugs are packaged in each packet.

It is preferable that the imaging unit captures the image of the drugs on a black background. According to this structure, the accuracy of the counting result of the number-by-appearance counting unit is improved.

Preferably, when capturing the image of the drugs after packaging, the imaging unit captures the image of the inside of the packet from a transparent side of the packet.

Preferably, the packaged drug inspection device according to the above-mentioned aspect further includes an impact giving unit that gives an impact to the drugs before the imaging unit captures the image of the drugs. According to this structure, the imaging unit is prevented from capturing the image of the drugs while the drugs overlap each other or rise vertically. Therefore, the accuracy of the counting result of the number-by-appearance counting unit is improved.

Preferably, the packaged drug inspection device according to the above-mentioned aspect further includes: a weight measurement unit that measures the weight of the drugs corresponding to each dose; a weight information acquisition unit that acquires weight information indicating the weight of the drugs corresponding to each dose, on the basis of at least the dispensing information and the drug type information; and a weight error determination unit that determines whether the weight of the drugs corresponding to each dose is correct, on the basis of the weight information and the measurement result of the weight measurement unit. Preferably, the packaging error determination unit determines whether the drugs packaged in each packet are correct, on the basis of the determination result of the weight error determination unit. According to this structure, it is possible to accurately determine whether the drugs packaged in each packet are correct.

In order to achieve the object of the invention, according to another aspect of the invention, there is provided a packaged drug inspection method including: a dispensing information acquisition step of acquiring dispensing information of drugs packaged in a packet; an inserted drug type information acquisition step of acquiring drug type information of the drugs inserted into a packaging machine which packages the drugs in the packet; an inserted drug type error determination step of determining whether the type of the drug inserted into the packaging machine is correct, on the basis of at least the dispensing information and the drug type information; a number-by-appearance information acquisition step of acquiring number-by-appearance information indicating the number of drugs for each outward appearance, which correspond to each dose and are packaged in each packet, on the basis of at least the dispensing information and the drug type information; an imaging step of capturing an image of the drugs corresponding to each dose; a number-by-appearance counting step of counting the number of drugs for each outward appearance, which correspond to each dose, on the basis of the image of the drugs captured in the imaging step; a number-by-appearance error determination step of determining whether the number of drugs for each outward appearance, which correspond to each dose, is correct, on the basis of the number-by-appearance information and the counting result in the number-by-appearance counting step; a mix-up determinability determination step of determining whether the occurrence or non-occurrence of a mix-up in which a different type of drug is put in the packet, instead of the drug to be put in the packet, can be determined, on the basis of at least the dispensing information and the drug type information; and a packaging error determination step of determining whether the drugs packaged in each packet are correct, on the basis of the determination result in the number-by-appearance error determination step and the determination result in the mix-up determinability determination step, and of determining that the drugs are correct when it is determined in the number-by-appearance error determination step that the number of drugs is correct and it is determined in the mix-up determinability determination step that the occurrence or non-occurrence of the mix-up can be determined.

The packaged drug inspection device and method according to the invention can accurately determine whether a packaged drug is correct at a low cost. Therefore, it is possible to reduce the burden of the pharmacist to dispensing inspection.

DESCRIPTION OF THE PREFERRED EMBODIMENTS

[Outline of Drug Prescribing Operation]

Figure 1:
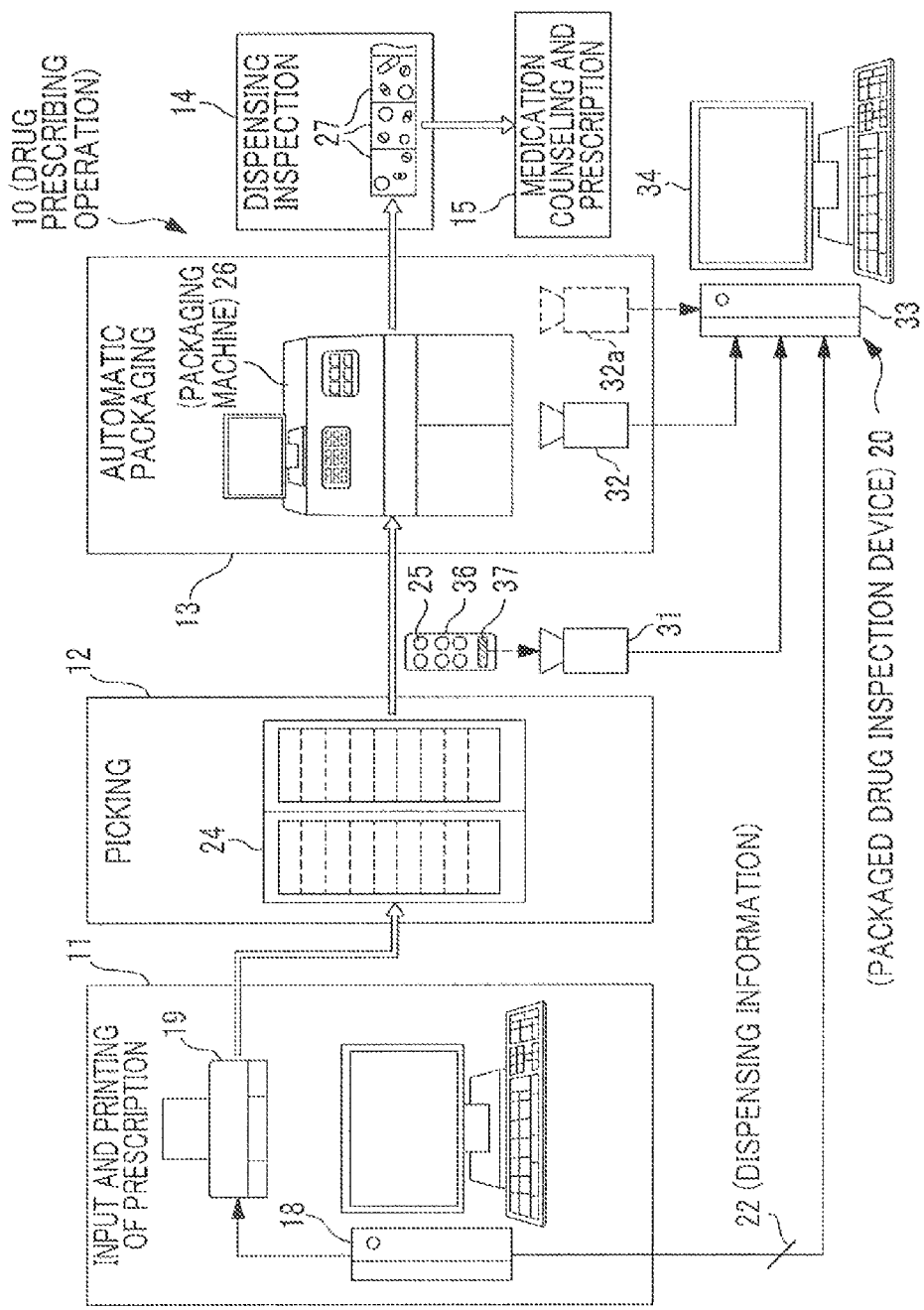
FIG. 1 is a diagram schematically illustrating a drug prescribing operation.

As illustrated in FIG. 1, a drug prescribing operation 10 which is performed in, for example, a hospital or a pharmacy mainly includes a prescription input and printing operation 11, a picking operation 12, an automatic packaging operation 13, a dispensing inspection operation 14, and a medication counseling and prescribing operation 15.

In the prescription input and printing operation 11, a pharmacist inputs dispensing information (for example, the name and age of a patient and the type (name), amount, usage, and dosage of drug) described in a prescription to a receipt computer 18. Then, the pharmacist operates the receipt computer 18 to print out the dispensing information from a printer 19 connected to the receipt computer 18. In addition, the receipt computer 18 outputs dispensing information 22 to a packaged drug inspection device 20.

In the picking operation 12, the pharmacist picks drugs (for example, pills and capsules) 25 corresponding to the dispensing information from a drug shelf 24, on the basis of the dispensing information output from the printer 19. In the picking operation 12, for example, an automatic picking device which automatically picks drugs on the basis of the dispensing information input to the receipt computer 18 may be used.

In the automatic packaging operation 13, the pharmacist sets the drugs 25 corresponding to each dose picked by the picking operation 12 on a tray of a packaging machine 26. Then, the packaging machine 26 automatically packages the drugs 25 on the tray in a plurality of packets 27. Since the packaging machine 26 is known, the detailed description of the structure thereof will not be repeated.

In the dispensing inspection operation 14, the pharmacist performs dispensing inspection which visually checks whether the type or number of drugs 25 packaged in each packet 27 is correct (that is, the type or number of drugs 25 is identical to that in the dispensing information 22).

In the medication counseling and prescribing operation 15, after dispensing inspection, the pharmacist instructs the patient on the use of drugs and prescribes the packaged drugs 25.

[Structure of Packaged Drug Inspection Device]

In the drug prescribing operation 10, the packaged drug inspection device 20 is used to determine whether the drugs 25 which have been packaged in each packet 27 by the packaging machine 26 are correct. Here, the "determining whether the drugs 25 are correct" means determining whether the type or number of drugs 25 which are one or more types and are packaged in each packet 27 is correct, is likely to be incorrect, and is incorrect on the basis of the dispensing information 22.

The packaged drug inspection device 20 mainly includes a first camera 31, a second camera (imaging unit) 32, an inspection device body 33, and a display unit (a first display unit, a second display unit, and a third display unit) 34.

The first camera 31 captures the image of drug type information 37 which is recorded on a package 36 (for example, a PTP sheet, a bottle, or a bin) of the drugs 25 picked by the pharmacist. The drug type information 37 is information indicating the type of drug, such as a barcode, characters, or electronic identification information recorded on an RF tag. When the drug type information 37 is a barcode, a barcode reader may be used as the first camera 31. When the drug type information 37 is electronic identification information recorded on an RF tag, an RF tag reader may be used as the first camera 31.

The second camera 32 captures the image of each drug 25 corresponding to a dose before packaging. For example, the second camera 32 captures the image of each of a plurality of drugs 25 corresponding to a dose which is set on the tray of the packaging machine 26. In FIG. 1, the second camera 32 is provided separately from the packaging machine 26. However, for example, the second camera 32 may be provided in the packaging machine 26.

The second camera 32 captures the image of the drugs 25 before packaging. However, for example, a second camera 32a may capture the image of the drugs 25 in each packet after packaging. The second camera 32a also corresponds to an imaging unit according to the invention and captures the image of the drugs 25 in the packet 27 through a transparent side surface of the packet 27.

The inspection device body 33 is, for example, a personal computer and is connected to the receipt computer 18, the first camera 31, and the second camera 32. The inspection device body 33 determines whether the drugs 25 packaged in each packet 27 are correct, on the basis of the dispensing information 22 input from the receipt computer 18 and image data input from the first camera 31 and the second camera 32. In addition, when it is determined that the drugs 25 packaged in each packet 27 are not correct, the inspection device body 33 outputs the determination result indicating that the drugs are incorrect to the display unit 34. In FIG. 1, the inspection device body 33 is provided separately from the packaging machine 26. However, for example, a computer (including a control unit) of the packaging machine may be used as the inspection device body 33.

The display unit 34 displays the determination result input from the inspection device body 33. For example, a monitor of the packaging machine 26 may be used as the display unit 34.

Figure 2:
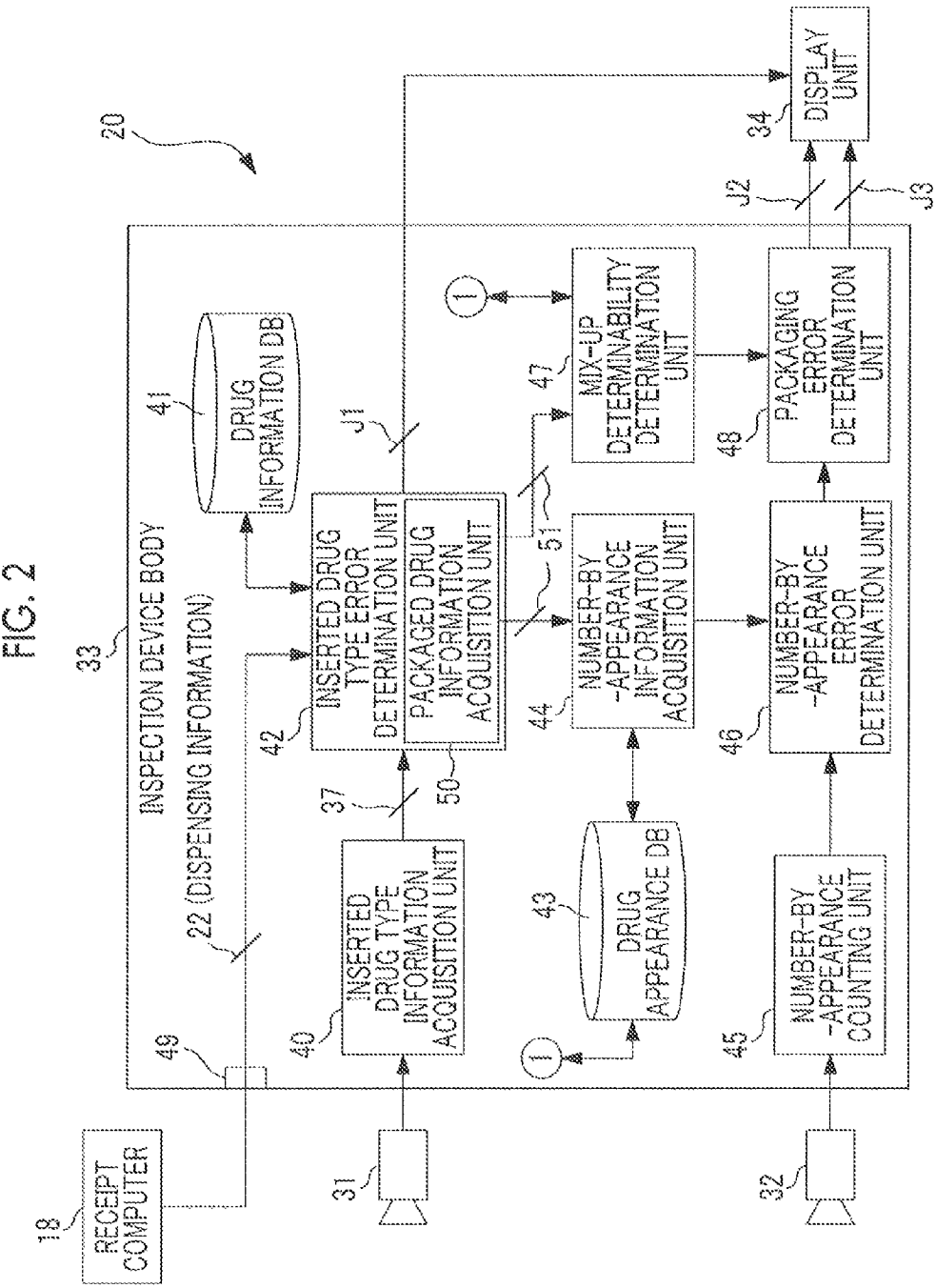
FIG. 2 is a block diagram illustrating the electrical structure of an inspection device body of a packaged drug inspection device.

As illustrated in FIG. 2, the inspection device body 33 includes an inserted drug type information acquisition unit 40, a drug information database (hereinafter, simply referred to as a drug information DB) 41, an inserted drug type error determination unit 42, a drug appearance database (hereinafter, simply referred to as a drug appearance DB) 43, a number-by-appearance information acquisition unit 44, a number-by-appearance counting unit 45, a number-by-appearance error determination unit 46, a mix-up determinability determination unit 47, a packaging error determination unit 48, and a communication interface (dispensing information acquisition unit) 49.

The inserted drug type information acquisition unit 40 forms an inserted drug type information acquisition unit according to the invention together with the first camera 31. The inserted drug type information acquisition unit 40 extracts, for example, at least one of the barcode and the characters recorded on the package 36 as the drug type information 37 from the image data (including read information of the barcode) of the drug type information 37 input from the first camera 31. Then, the inserted drug type information acquisition unit 40 outputs the drug type information 37 to the inserted drug type error determination unit 42. In this embodiment, the inserted drug type information acquisition unit 40 is provided in the inspection device body 33. However, the inserted drug type information acquisition unit 40 may be provided in the first camera 31.

Figure 3:
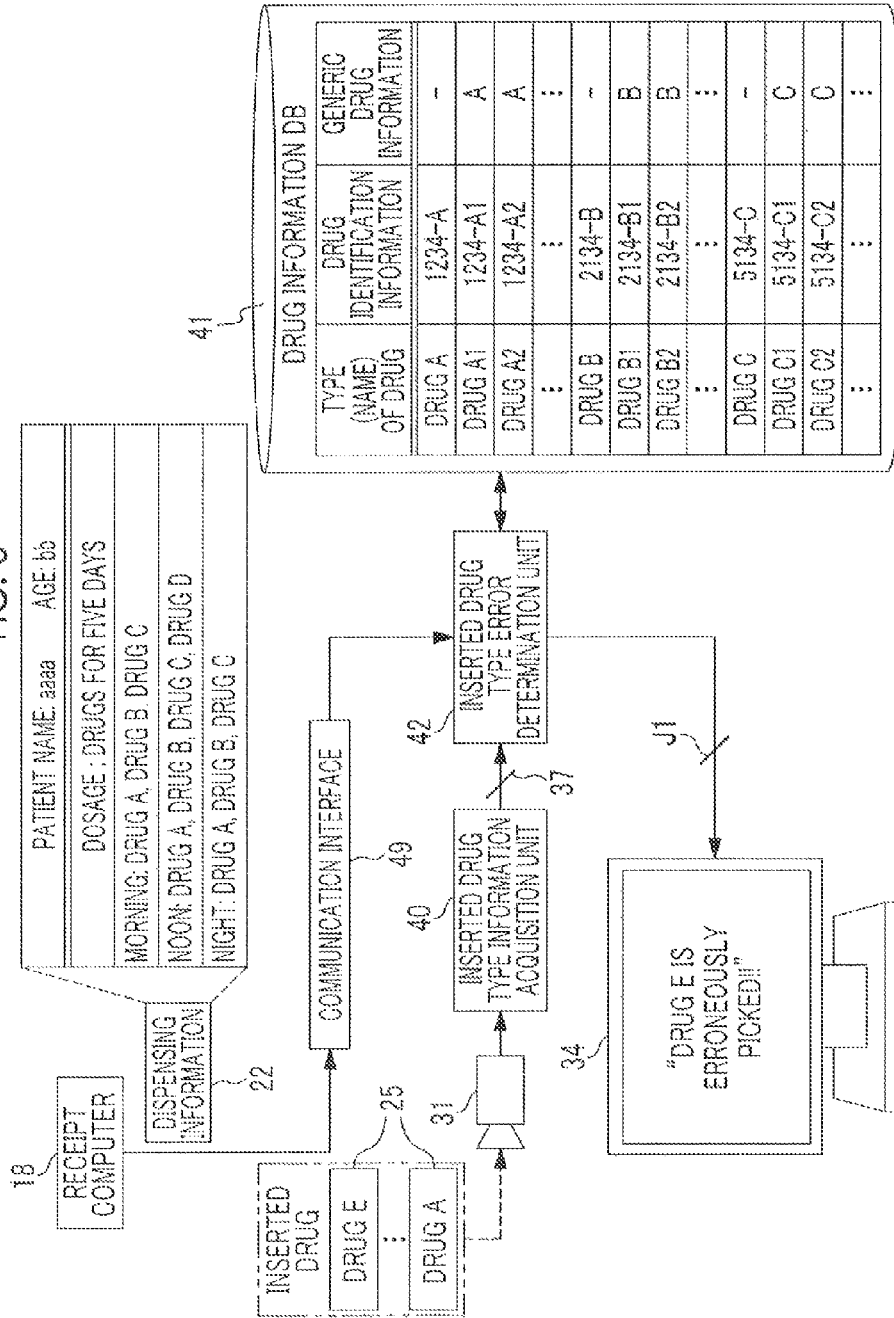
FIG. 3 is a diagram illustrating an error determination process performed by an inserted drug type error determination unit.

As illustrated in FIG. 3, the type of the drug 25, the drug type information 37, and generic drug information indicating the correspondence relationship between an original drug and a generic drug are stored in the drug information DB 41 in advance so as to be associated with each other. In FIG. 3, "A, A1, A2, . . . , B, B1, B2, . . . , C, C1, C2, . . . " described in a drug type field indicates the types of the drugs 25. In addition, drugs A1 and A2 are the generic drugs of a drug A, drugs B1 and B2 are the generic drugs of a drug B, and drugs C1 and C2 are the generic drugs of a drug C. Hereinafter, when drugs are described as the drugs 25, the drugs include all types of drugs. When drugs are described as the drugs A, B, . . . , the drugs include these types of drugs.

In FIG. 3, the drug type information 37 of the package 36 is recorded in a "drug identification information" field. When the drug 25 is a generic drug, the type of the original drug of the drug 25 (or the drug type information 37) is recorded in a "generic drug information" field. The type of the drug 25 becomes clear from the drug type information 37 with reference to the drug information DB 41 and it is possible to distinguish the original drug or the generic drug (a drug having the same active ingredients) of the drug 25.

The inserted drug type error determination unit 42 determines whether the type of the drug 25 inserted into the packaging machine 26 is correct, on the basis of the dispensing information 22 which is input from the receipt computer 18 through the communication interface 49 and the drug type information 37 input from the inserted drug type information acquisition unit 40, with reference to the drug information DB 41.

Specifically, the inserted drug type error determination unit 42 determines the type of the drug 25 to be inserted into the packaging machine 26 on the basis of the dispensing information 22. In addition, the inserted drug type error determination unit 42 determines the type of the drug 25 (which is represented as an inserted drug in FIG. 3) which is picked by the picking operation 12 and is then inserted into the packaging machine 26, on the basis of the drug type information 37, with reference to the drug information DB 41. Then, the inserted drug type error determination unit 42 determines whether the type of the drug 25 inserted into the packaging machine 26 is correct, on the basis of the type of the drug 25 designated by the dispensing information 22 and the type of the drug 25 inserted into the packaging machine 26. When the type of each drug 25 inserted into the packaging machine 26 is the same as the type of the drug 25 designated by the dispensing information 22, the inserted drug type error determination unit 42 determines that the type of the drug 25 is correct. However, when the types of the drugs are different from each other, the inserted drug type error determination unit 42 determines that the type of the drug 25 is not correct.

At that time, when the drug 25 corresponding to the drug type information 37 is a generic drug (or an original drug) having the same active ingredients as the drug 25 designated by the dispensing information 22, the inserted drug type error determination unit 42 determines that the drug type is correct even though the drug types are different from each other. In addition, when the drug 25 corresponding to the drug type information 37 is not a generic drug of the drug 25 designated by the dispensing information 22 and has the same type, effect, and active ingredients as the drug 25 designated by the dispensing information 22, the inserted drug type error determination unit 42 determines that the drug type is correct. In this case, information indicating the correspondence relationship between the drugs which have the same type and effect is stored in the drug information DB 41 in advance.

When it is determined that the type of the drug 25 inserted into the packaging machine 26 is not correct, the inserted drug type error determination unit 42 outputs a determination result J1 including information about the corresponding drug type to the display unit 34. Then, the display unit 34 displays information indicating that the type of the drug 25 inserted into the packaging machine 26 is not correct and the type of the drug 25. For example, when the first camera 31 captures the image of the drug type information 37 of the package 36 including a drug 25 (here, a drug E) which is not designated by the dispensing information 22, the inserted drug type error determination unit 42 outputs the determination result J1 indicating that the "drug E" is incorrect to the display unit 34. Then, the display unit 34 displays, for example, warning information indicating that the "drug E is erroneously picked". The display aspect of the warning information may be appropriately changed.

Returning to FIG. 2, the inserted drug type error determination unit 42 is provided with a packaged drug information acquisition unit 50. The packaged drug information acquisition unit 50 acquires packaged drug information 51 indicating the types of drugs 25 which are packaged in each packet 27 (packet 1, packet 2, . . . ) by the packaging machine 26 and the number of drugs for each type, on the basis of the dispensing information 22 and the drug type information 37 of each of the picked drugs 25, with reference to the drug information DB 41 (see FIG. 4). The packaged drug information acquisition unit 50 outputs the packaged drug information 51 to the number-by-appearance information acquisition unit 44 and the mix-up determinability determination unit 47.

Figure 4:
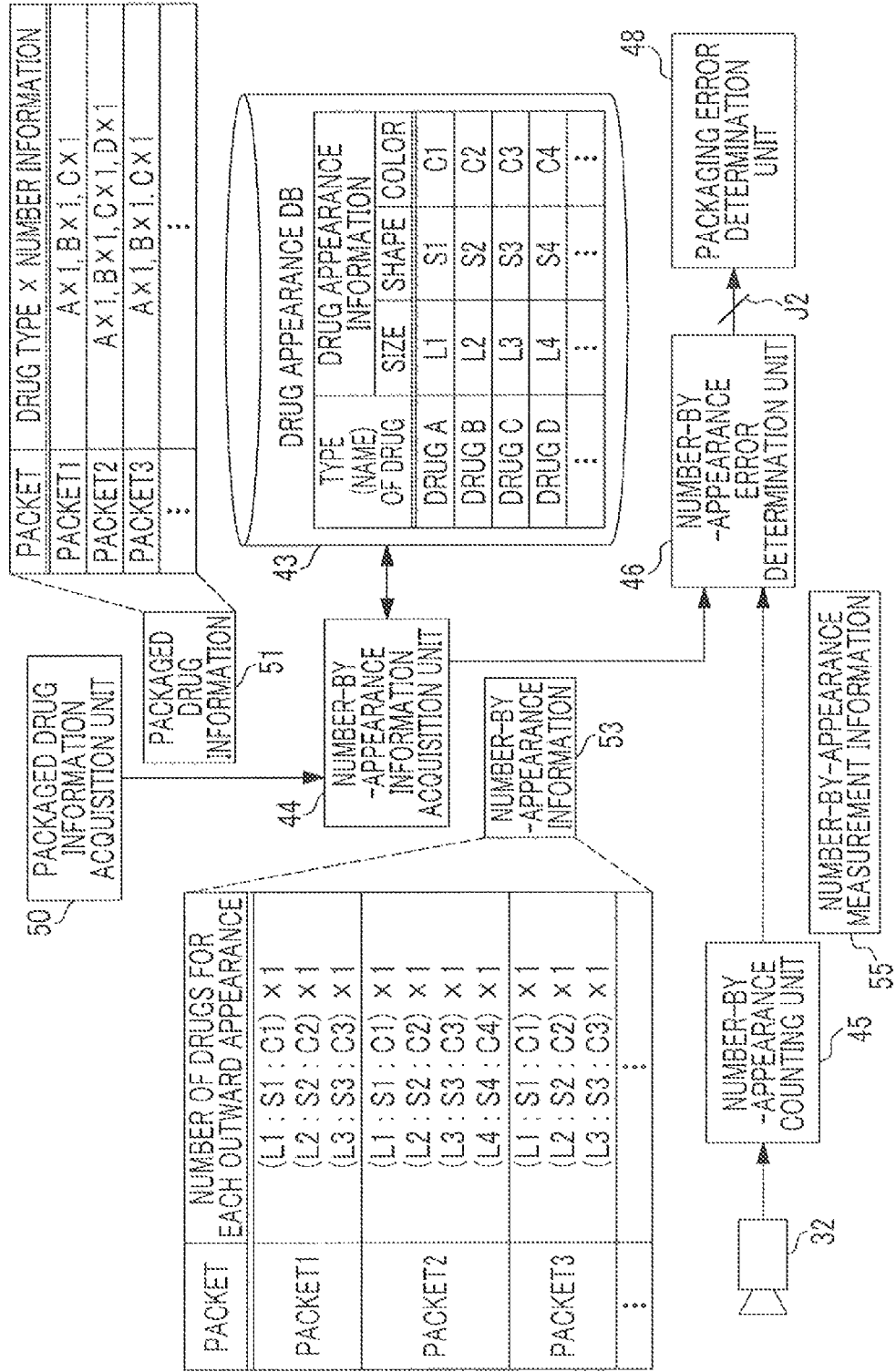
FIG. 4 is a diagram illustrating an error determination process performed by a number-by-appearance error determination unit.

As illustrated in FIG. 4, the type of each drug 25 and drug appearance information indicating the outward appearance of the drug are stored in the drug appearance DB 43 so as to be associated with each other. The drug appearance information includes information indicating the size (for example, an area, a diameter, and the length of a major axis and/or a minor axis), shape (for example, a circular shape, a triangular shape, an elliptical shape, and a capsule shape), and color (for example, RGB values) of the drug 25. In addition, L1, L2, L3, L4, . . . indicating the sizes of the drugs A, B, C, D, . . . , S1, S2, S3, S4, . . . indicating the shapes of the drugs A, B, C, D, . . . , and C1, C2, C3, C4, . . . indicating the colors of the drugs A, B, C, D, . . . are known values.

The number-by-appearance information acquisition unit 44 acquires number-by-appearance information 53 indicating the number of drugs 25 for each outward appearance (number by appearance) which are packaged in each packet 27, on the basis of the packaged drug information 51 input from the packaged drug information acquisition unit 50, with reference to the drug appearance DB 43. For example, when the packaged drug information 51 corresponding to the packet 27, which is "packet 1", is "A×1, B×1, C×1", the number-by-appearance information acquisition unit 44 determines the number-by-appearance information 53 of "packet 1", with reference to the drug appearance information corresponding to the drugs A, B, and C in the drug appearance DB 43. In this case, the number-by-appearance information 53 of "packet 1" is "(L1:S1:C1)×1, (L2:S2:C2)×1, (L3:S3:C3)×1)". Therefore, it is determined that one drug 25 satisfying an outward appearance (L1:S1:C1), one drug 25 satisfying an outward appearance (L2:S2:C2), and one drug 25 satisfying an outward appearance (L3:S3:C3) are included in the packet 27 which is packet 1.

Similarly, the number-by-appearance information acquisition unit 44 determines the number-by-appearance information 53 corresponding to the packets 27 which are "packet 2, packet 3, . . . ". Then, the number-by-appearance information acquisition unit 44 outputs the number-by-appearance information 53 of each packet 27 to the number-by-appearance error determination unit 46. In this embodiment, the number-by-appearance information acquisition unit 44 acquires the number-by-appearance information 53 on the basis of the packaged drug information 51 acquired from the packaged drug information acquisition unit 50. However, the number-by-appearance information acquisition unit 44 may have the function of the packaged drug information acquisition unit 50. That is, the packaged drug information acquisition unit 50 may not be provided and the number-by-appearance information acquisition unit 44 may acquire the packaged drug information 51 on the basis of the dispensing information 22 and the drug type information 37 acquired from, for example, the inserted drug type error determination unit 42, with reference to the drug information DB 41. In this case, the number-by-appearance information acquisition unit 44 can acquire the number-by-appearance information 53 on the basis of at least the dispensing information 22 and the drug type information 37.

The number-by-appearance counting unit 45 analyzes the image data of the drugs 25 corresponding to each packet (packet 1, packet 2, . . . ) before packaging, which is input from the second camera 32, and counts the number of drugs 25 for each outer appearance which are packaged in each packet 27. That is, the number-by-appearance counting unit 45 counts the number of drugs 25 for each item corresponding to the drug appearance information (a size, a shape, and a color). The number-by-appearance counting unit 45 may be provided integrally with the second camera 32.

Specifically, the number-by-appearance counting unit 45 can perform a known edge extraction process or a known segmentation process for the image data to extract the contour of the drug 25 in the image and determine the size and shape of the drug 25 in the image. When the image data is color image data, the number-by-appearance counting unit 45 can distinguish the color of the drug 25 in the image on the basis of the image data. A method for counting the number of drugs 25 for each outer appearance on the basis of the image data is not particularly limited. For example, various known methods may be used. The number-by-appearance counting unit 45 outputs number-by-appearance measurement information (hereinafter, simply referred to as measurement information) 55 indicating the counting result of the number of drugs for each outward appearance to the number-by-appearance error determination unit 46.

The measurement information 55 basically has the same format as the number-by-appearance information 53. The counting result for each packet "outward appearance 1 (size, shape, and color)×the number of drugs, outward appearance 2 (size, shape, and color)×the number of drugs, . . . " is recorded in the measurement information 55.

The number-by-appearance error determination unit 46 checks the number-by-appearance information 53 input from the number-by-appearance information acquisition unit 44 and the measurement information 55 input from the number-by-appearance counting unit 45. Then, the number-by-appearance error determination unit 46 determines whether the number of drugs 25 for each outward appearance, which are packaged in each packet 27, is correct, on the basis of whether the measurement information 55 is identical to the number-by-appearance information 53, and outputs a determination result J2 to the packaging error determination unit 48. At that time, when the number of drugs 25 for each outward appearance, which are packaged in the packet 27, is incorrect, the number-by-appearance error determination unit 46 outputs the determination result J2 including information indicating the packet 27 to the packaging error determination unit 48.

Figure 5:
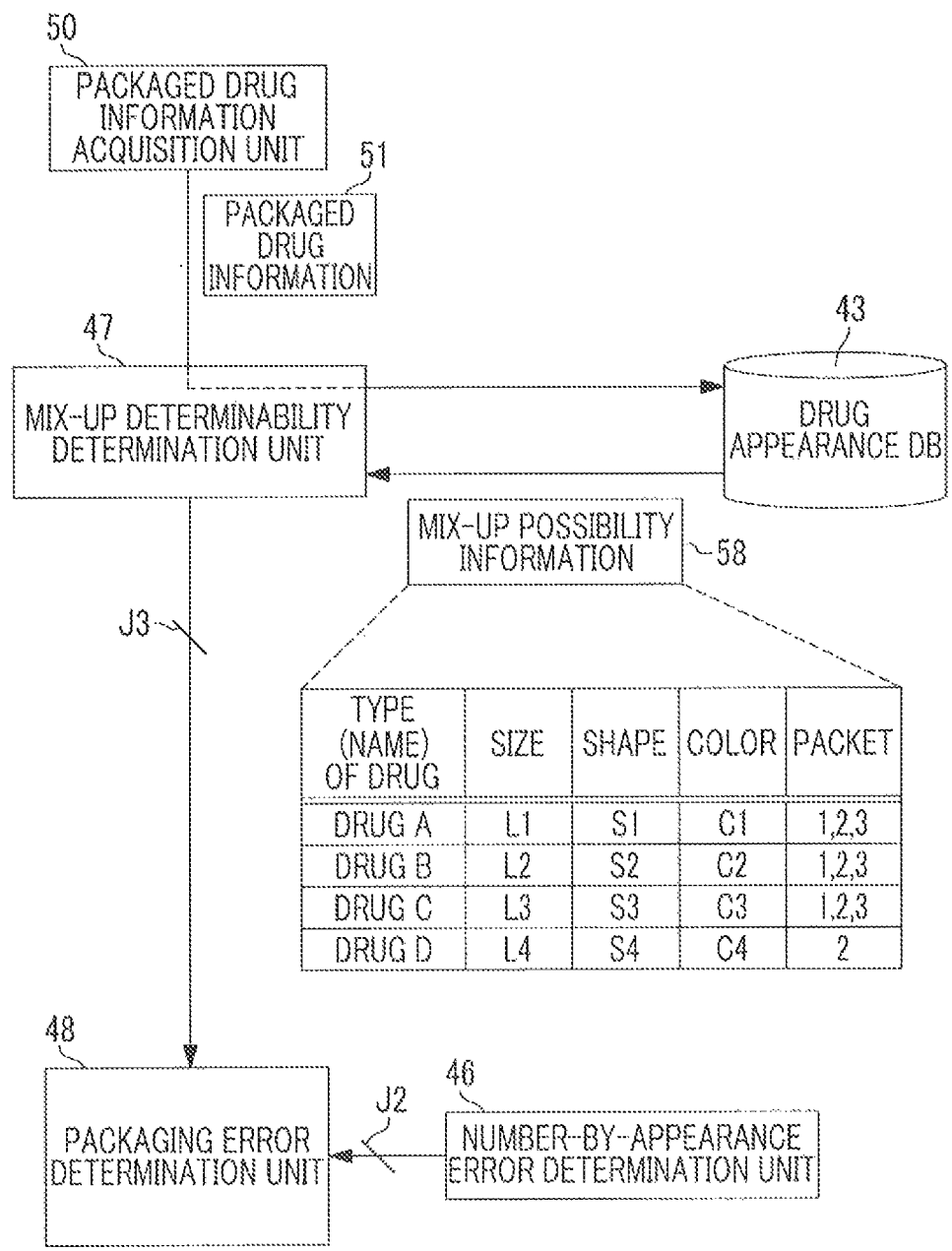
FIG. 5 is a diagram illustrating a determination process performed by a mix-up determinability determination unit.

As illustrated in FIG. 5, the mix-up determinability determination unit 47 determines whether the mix-up of the drugs 25 can be determined, on the basis of the packaged drug information 51 input from the packaged drug information acquisition unit 50, with reference to the drug appearance DB 43.

Figure 6A:
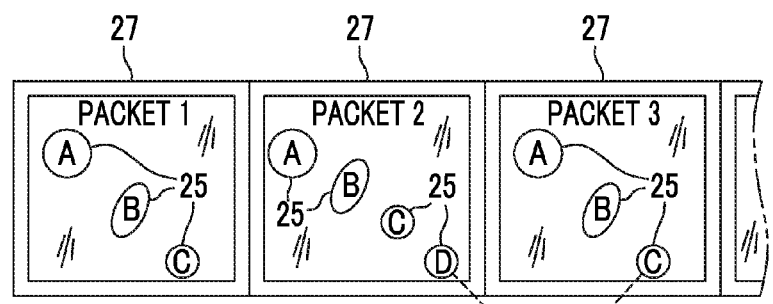
FIGS. 6A and 6B are diagrams illustrating a mix-up of drugs.
Figure 6B:
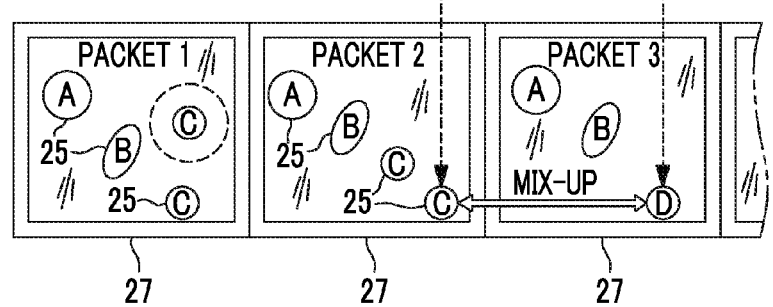

As illustrated in FIGS. 6A and 6B, the "mix-up" of the drugs 25 means that a drug 25 (except for an original drug and a generic drug) which is a different type from the drug 25 to be put in each packet 27 is put in the packet 27. Specifically, the mix-up of the drugs between the packets occurs. For example, a "drug D" to be put in the packet 27, which is packet 2, is put in the packet 27, which is packet 3, and a "drug C" to be put in the packet 27, which is packet 3, is put in the packet 27 which is packet 2. In addition, the "mix-up" does not occur only between the packets. In addition, the mix-up of the drugs in the same packet occurs. For example, the "drug C" is put in the packet 27, which is the packet 2, instead of the "drug D" to be put in the packet 27 and the "drug D" is not put in any other packet 27. The "mix-up" occurs due to, for example, an error in the setting of the drugs 25 to the tray of the packaging machine 26 by the pharmacist or an error in the packaging machine 26.

"Whether the occurrence or non-occurrence of the mix-up can be determined" means whether the occurrence or non-occurrence of the "mix-up" can be determined from the outward appearance of the drug 25. For example, as illustrated in FIG. 6B, in the case in which the mix-up of the "drug C" and the "drug D" occurs in the packets 27 which are packet 2 and packet 3, when the "drug C" and the "drug D" have different outward appearances, the number-by-appearance error determination unit 46 determines that the number of drugs 25 for each outward appearance which are packaged in the packets 27, which are packet 2 and packet 3, is incorrect. Therefore, in this case, it is possible to determine whether the mix-up occurs. FIG. 6B illustrates an example in which the drug C is additionally put in the packet 27 which is packet 1.

On the other hand, when the "drug C" and the "drug D" have the same or similar outward appearance, the number-by-appearance counting unit 45 is less likely to distinguish the "drug C" and the "drug D" and to count the drugs. In this case, even when the mix-up of the "drug C" and the "drug D" occurs, it is difficult for the number-by-appearance error determination unit 46 to accurately determine whether the number of drugs 25 for each outward appearance is correct since the mix-up is not reflected in the measurement information 55. Therefore, in this case, it is difficult to determine whether the mix-up occurs. As a result, even when the number-by-appearance error determination unit 46 determines that the number of drugs for each outward appearance is correct, the mix-up of different types of drugs 25 is likely to occur. As such, "whether the occurrence or non-occurrence of the mix-up can be determined" is determined on the basis of whether two or more types of drugs 25 having the same or similar outward appearance are included in the drugs 25 inserted into the packaging machine 26.

Returning to FIG. 5, the mix-up determinability determination unit 47 acquires mix-up possibility information 58 indicating whether the occurrence or non-occurrence of the mix-up of the drugs 25 can be determined, on the basis of the packaged drug information 51 input from the packaged drug information acquisition unit 50, with reference to the drug appearance DB 43. Specifically, the mix-up determinability determination unit 47 acquires drug appearance information corresponding to each drug 25 in the packaged drug information 51, on the basis of the packaged drug information 51, with reference to the drug appearance DB 43. In addition, information indicating which of the packets 27 (packet 1, packet 2, . . . ) the drug 25 is inserted into is stored in a "packet" field of the mix-up possibility information 58.

Then, the mix-up determinability determination unit 47 determines whether the occurrence or non-occurrence of the mix-up of the drugs 25 packaged in each packet 27 can be determined, on the basis of the mix-up possibility information 58. Specifically, the mix-up determinability determination unit 47 determines whether the outward appearances of different types of drugs 25 (different types of drugs 25 between the packets) inserted into different packets 27 satisfy the following first to third conditions. The number of conditions varies depending on the number of parameters (a size, a shape, and a color) for the number of drugs for each outward appearance.

The first condition is that the difference between the shapes of different types of drugs 25 is small. For example, in a case in which the shapes of different types of drugs 25 are represented by the difference between the diameters of a circumscribed circle and an inscribed circle, when the difference between the drugs is less than 0.1 mm, the mix-up determinability determination unit 47 determines that the difference between the shapes of different types of drugs 25 is small. Alternatively, in a case in which the shapes of different types of drugs 25 are represented by the maximum difference between the circumscribed circle and the outer edge, when the difference between the drugs is less than 0.1 mm, the mix-up determinability determination unit 47 determines that the difference between the shapes of different types of drugs 25 is small.

The second condition is that the difference between the sizes of different types of drugs 25 is small. For example, the mix-up determinability determination unit 47 determines that the difference between the sizes of the drugs 25 is small when the difference between the diameters of different types of drugs 25 is less than 0.1 mm or when the difference between the shortest distances from the centers (points at which the sum of the distances from the circumference of the outer edge is the shortest) to the outer circumferences of the drugs 25 is less than 0.05 mm.

The third condition is that the difference between the colors and brightnesses of different types of drugs 25 is small. For example, the mix-up determinability determination unit 47 determines that the difference between the colors and brightnesses of different types of drugs 25 is small when the color difference ($\Delta E$) between the drugs under a standard light source is less than 2.0 or when the difference between the RGB values of the drugs is less than 10% in all colors. In addition, the color difference may be calculated by a known technique defined by the International Commission on Illumination (CIE).

The mix-up determinability determination unit 47 determines that the occurrence or non-occurrence of the mix-up of different types of drugs 25 cannot be determined, on the basis of the mix-up possibility information 58, when the outward appearances of different types of drugs 25 inserted into different packets 27 satisfy the first to third conditions. Then, when the occurrence or non-occurrence of the mix-up of different types of drugs 25 cannot be determined, the mix-up determinability determination unit 47 generates a determination result J3 (see FIG. 8) including the types of drugs 25 which are different in type.

On the other hand, when the outward appearances of different types of drugs 25 inserted into different packets 27 do not satisfy one of the first to third conditions, the mix-up determinability determination unit 47 determines that the occurrence or non-occurrence of the mix-up can be determined and generates a determination result J3.

The mix-up determinability determination unit 47 determines whether the outward appearances of different types of drugs 25 inserted into the same packet 27 satisfy the first to third conditions and generates the determination result J3. When the mix-up determinability determination unit 47 determines that the occurrence or non-occurrence of the mix-up of different types of drugs 25 cannot be determined, the types of drugs 25 which are different in type are included in the determination result J3.

The mix-up determinability determination unit 47 outputs the determination result J3 to the packaging error determination unit 48. In this embodiment, the mix-up determinability determination unit 47 acquires the mix-up possibility information 58 on the basis of the packaged drug information 51 acquired from the packaged drug information acquisition unit 50 and determines whether the occurrence or non-occurrence of the mix-up of the drugs 25 can be determined. However, the mix-up determinability determination unit 47 may have the function of the packaged drug information acquisition unit 50. That is, the packaged drug information acquisition unit 50 may not be provided and the mix-up determinability determination unit 47 may acquire the mix-up possibility information 58 with reference to the drug appearance DB 43, on the basis of the dispensing information 22 and the drug type information 37 acquired from, for example, the inserted drug type error determination unit 42. In this case, the mix-up determinability determination unit 47 can determine whether the occurrence or non-occurrence of the mix-up of the drugs 25 can be determined on the basis of at least the dispensing information 22 and the drug type information 37.

The packaging error determination unit 48 determines whether the drugs 25 packaged in each packet 27 are correct, on the basis of the determination result J2 of the number-by-appearance error determination unit 46 and the determination result J3 of the mix-up determinability determination unit 47. Specifically, when the number of drugs 25 for each outward appearance which are packaged in each packet 27 is correct and the occurrence or non-occurrence of the mix-up of the drugs 25 can be determined, the packaging error determination unit 48 determines that the drugs 25 packaged in each packet 27 are correct.

Figure 7:
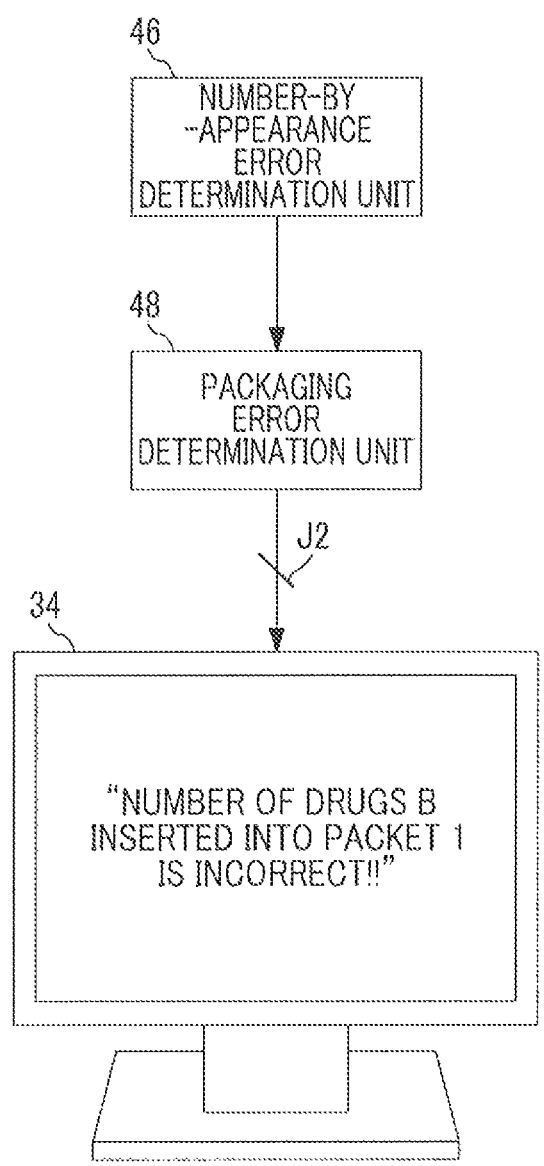
FIG. 7 is a diagram illustrating an example of the display of a warning when the number-by-appearance error determination unit determines that the number of drugs is incorrect.

On the other hand, when the number of drugs 25 for each outward appearance which are packaged in each packet 27 is not correct, the packaging error determination unit 48 determines that the drugs 25 packaged in the packet 27 are not correct. Then, as illustrated in FIG. 7, the packaging error determination unit 48 outputs the determination result J2 indicating the packet 27 in which the number of drugs for each outward appearance is not correct to the display unit 34. Then, warning information indicating the packet 27 (for example, packet 1 illustrated in FIG. 6B) in which the number of drugs for each outward appearance is not correct is displayed on the display unit 34.

Figure 8:
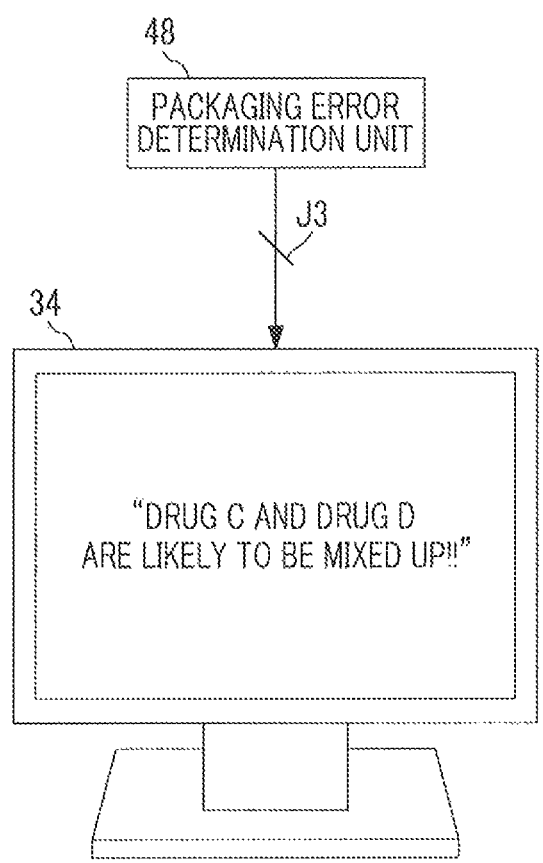
FIG. 8 is a diagram illustrating an example of the display of a warning when the mix-up determinability determination unit determines that the occurrence or non-occurrence of the mix-up cannot be determined.

When the occurrence or non-occurrence of the mix-up of different types of drugs 25 cannot be determined, the packaging error determination unit 48 determines that the drugs 25 packaged in each packet 27 are likely to be incorrect. Then, as illustrated in FIG. 8, the packaging error determination unit 48 outputs the determination result J3 indicating the type of the drug 25 whose mix-up cannot be determined to the display unit 34. Then, warning information indicating the types of the drugs 25 whose mix-up cannot be determined (for example, the drug C and the drug D illustrated in FIG. 6B) is displayed on the display unit 34.

When the number of drugs 25 for each outward appearance which are packaged in each packet 27 is not correct and the occurrence or non-occurrence of the mix-up of different types of drugs 25 cannot be determined, warning information illustrated in FIG. 7 and FIG. 8 is displayed on the display unit 34.

[Operation of Packaged Drug Inspection Device]

Figure 9:
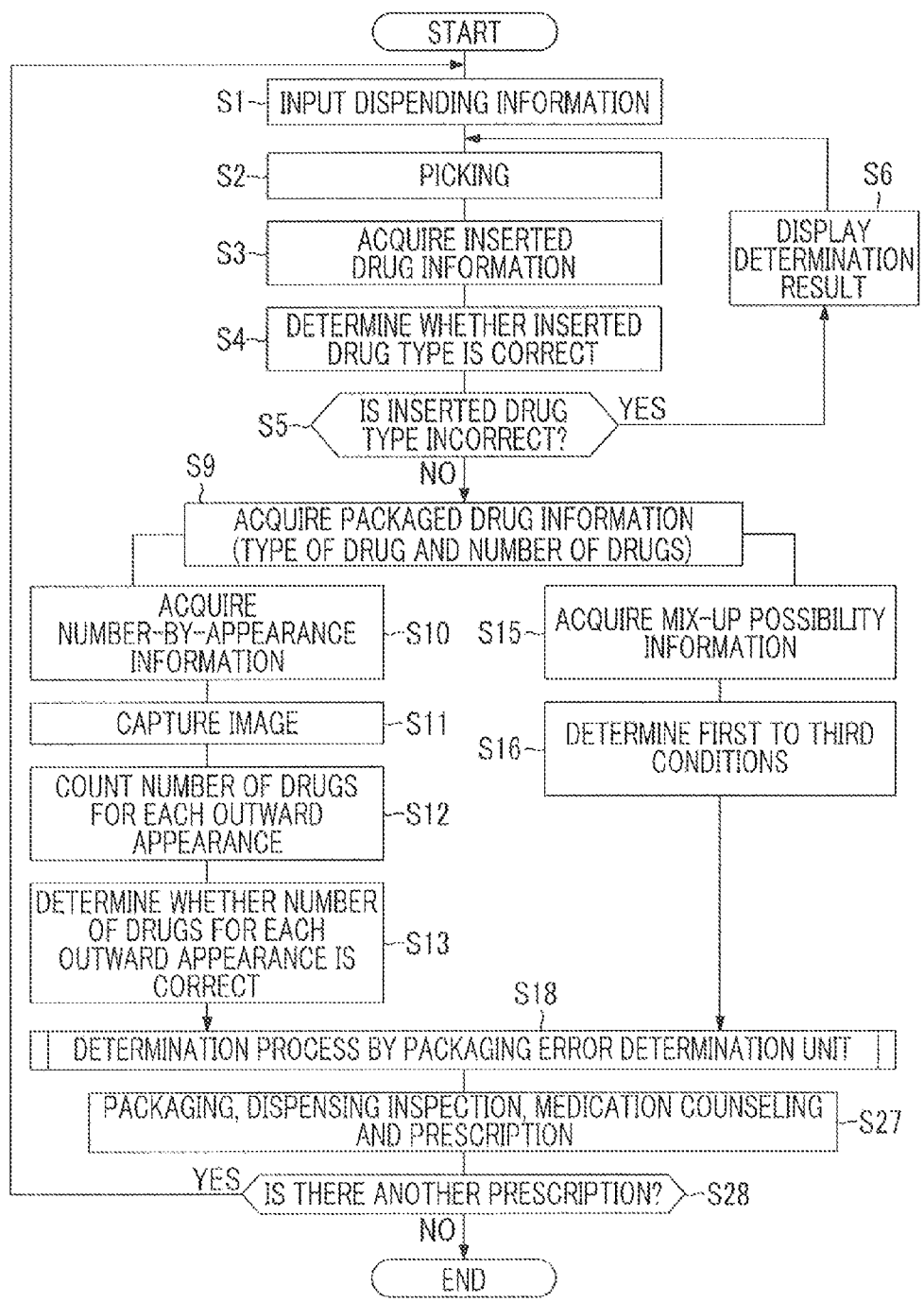
FIG. 9 is a flowchart illustrating the flow of an inspection process of the packaged drug inspection device in the drug prescribing operation.

Next, the operation of the packaged drug inspection device 20 having the above-mentioned structure will be described with reference to FIG. 9. When the pharmacist receives a prescription, the drug prescribing operation 10 starts. At the beginning, in the prescription input and printing operation 11, the pharmacist inputs the dispensing information 22 described in the prescription to the receipt computer 18 and prints out the dispensing information 22 using the printer 19 (Step S1). In addition, the receipt computer 18 outputs the dispensing information 22 input by the pharmacist to the packaged drug inspection device 20. In this way, the packaged drug inspection device 20 can acquire the dispensing information 22 (dispensing information acquisition step).

The pharmacist performs the picking operation 12 of picking the drugs 25 which correspond to the dispensing information 22 output from the printer 19 from the drug shelf 24 (Step S2).

After the picking operation 12, the pharmacist sets the package 36 of each of the picked drugs 25 in front of the first camera 31 and the first camera 31 is used to capture the image of the drug type information 37 of each drug 25. The first camera 31 outputs the image data of each drug type information item 37 to the inserted drug type information acquisition unit 40. The inserted drug type information acquisition unit 40 extracts the drug type information 37 from the image data. In this way, the inserted drug type information acquisition unit 40 acquires the drug type information 37 of each drug 25 picked by the pharmacist (Step S3; an inserted drug type information acquisition step). The inserted drug type information acquisition unit 40 outputs the drug type information 37 to the inserted drug type error determination unit 42.

As illustrated in FIG. 3, the inserted drug type error determination unit 42 determines whether the type of drug 25 inserted into the packaging machine 26 is correct, with reference to the drug information DB 41, on the basis of the drug type information 37 and the dispensing information 22 which is input in advance from the receipt computer 18 through the communication interface 49 (Step S4; an inserted drug type error determination step). Then, when the type of each drug 25 inserted into the packaging machine 26 is the same as the type of drug 25 designated by the dispensing information 22 or is an original drug or a generic drug having the same active ingredients as the drug 25, the inserted drug type error determination unit 42 determines that the type of drug 25 inserted into the packaging machine 26 is correct (NO in Step S5).

On the other hand, when the type of each drug 25 inserted into the packaging machine 26 is not the same as the type of drug 25 designated by the dispensing information 22 or is not an original drug or a generic drug, the inserted drug type error determination unit 42 determines that the type of drug 25 inserted into the packaging machine 26 is not correct (YES in Step S5). In this case, the inserted drug type error determination unit 42 outputs the determination result J1 including information about the corresponding drug type to the display unit 34. As a result, as illustrated in FIG. 3, the display unit 34 displays information indicating that the type of drug 25 inserted into the packaging machine 26 is not correct and the drug type (Step S6). Therefore, it is possible to warn the pharmacist that an error has occurred in the picking operation 12 and to prompt the pharmacist to correct the picking operation 12.

Until the inserted drug type error determination unit 42 determines that the type of each drug 25 inserted into the packaging machine 26 is correct (NO in Step S5), the process from Step S2 to Step S6 is repeatedly performed. Even when the inserted drug type error determination unit 42 determines that the types of all of the drugs 25 are correct, the determination result may be displayed on the display unit 34. After the drug type is checked, the pharmacist extracts the picked drugs 25 from the package 36 and sets each dose of drug on the tray of the packaging machine 26.

Then, the packaged drug information acquisition unit 50 acquires the packaged drug information 51 (the type of drug and the number of drugs for each type) of each drug 25 corresponding to a dose, with reference to the drug information DB 41, on the basis of the dispensing information 22 and the drug type information 37 of each drug 25 (Step S9). Then, the packaged drug information acquisition unit 50 outputs the packaged drug information 51 to the number-by-appearance information acquisition unit 44 and the mix-up determinability determination unit 47.

<Process of Determining Number of Drugs for Each Outward Appearance>

As illustrated in FIG. 4, the number-by-appearance information acquisition unit 44 acquires the number-by-appearance information 53 of the drugs 25 packaged in each packet 27, on the basis of the packaged drug information 51 input from the packaged drug information acquisition unit 50, with reference to the drug appearance DB 43 (Step S10; a number-by-appearance information acquisition step). Then, the number-by-appearance information acquisition unit 44 outputs the number-by-appearance information 53 to the number-by-appearance error determination unit 46.

The second camera 32 captures the image of each of the drugs 25 corresponding to each dose, which are set on the tray of the packaging machine 26, and outputs the image data of the drugs 25 corresponding to each dose to the number-by-appearance counting unit 45 (Step S11; an imaging step). The number-by-appearance counting unit 45 analyzes the image data of the drugs 25 corresponding to each dose to count the number of drugs 25 for each outward appearance, which correspond to each dose, and outputs the measurement information 55 indicating the counting result to the number-by-appearance error determination unit 46 (Step S12; a number-by-appearance counting step).

The number-by-appearance error determination unit 46 checks the number-by-appearance information 53 input from the number-by-appearance information acquisition unit 44 and the measurement information 55 input from the number-by-appearance counting unit 45 and determines whether the number of drugs 25 for each outward appearance which are packaged in each packet 27 is correct (Step S13; a number-by-appearance error determination step). Then, when the number of drugs 25 for each outward appearance which are packaged in each packet 27 is correct, the number-by-appearance error determination unit 46 outputs the determination result J2 indicating that the number of drugs 25 is correct to the packaging error determination unit 48. On the other hand, when the number of drugs 25 is not correct, the number-by-appearance error determination unit 46 outputs information indicating that the number of drugs 25 is not correct and the determination result J2 indicating the corresponding packet 27 to the packaging error determination unit 48.

<Determination of First to Third Conditions>

At the same time as the number-by-appearance determination process (from Step S10 to Step S13) or before or after the number-by-appearance determination process, the mix-up determinability determination unit 47 acquires the mix-up possibility information 58 illustrated in FIG. 5, on the basis of the packaged drug information 51 input from the packaged drug information acquisition unit 50, with reference to the drug appearance DB 43 (Step S15).

The mix-up determinability determination unit 47 determines whether the outward appearances of different types of drugs 25 inserted into different packets 27 or the same packet 27 satisfy the first to third conditions (the difference between the shapes, the difference between the sizes, and the difference between colors and brightnesses), on the basis of the mix-up possibility information 58 (Step S16). When the occurrence or non-occurrence of the mix-up of different types of drugs 25 can be determined, the mix-up determinability determination unit 47 generates the determination result J3 indicating that the occurrence or non-occurrence of the mix-up can be determined. When the occurrence or non-occurrence of the mix-up of different types of drugs 25 cannot be determined, the mix-up determinability determination unit 47 generates the determination result J3 including the types of the drugs 25 which are different in type. Then, the mix-up determinability determination unit 47 outputs the determination result J3 to the mix-up determinability determination unit 47.

<Determination Process by Packaging Error Determination Unit>

The packaging error determination unit 48 acquires the determination result J2 of the number-by-appearance error determination unit 46 and the determination result J3 of the mix-up determinability determination unit 47 and determines whether the drugs 25 packaged in each packet 27 are correct on the basis of the determination results J2 and J3 (Step S18; a packaging error determination step).

Figure 10:
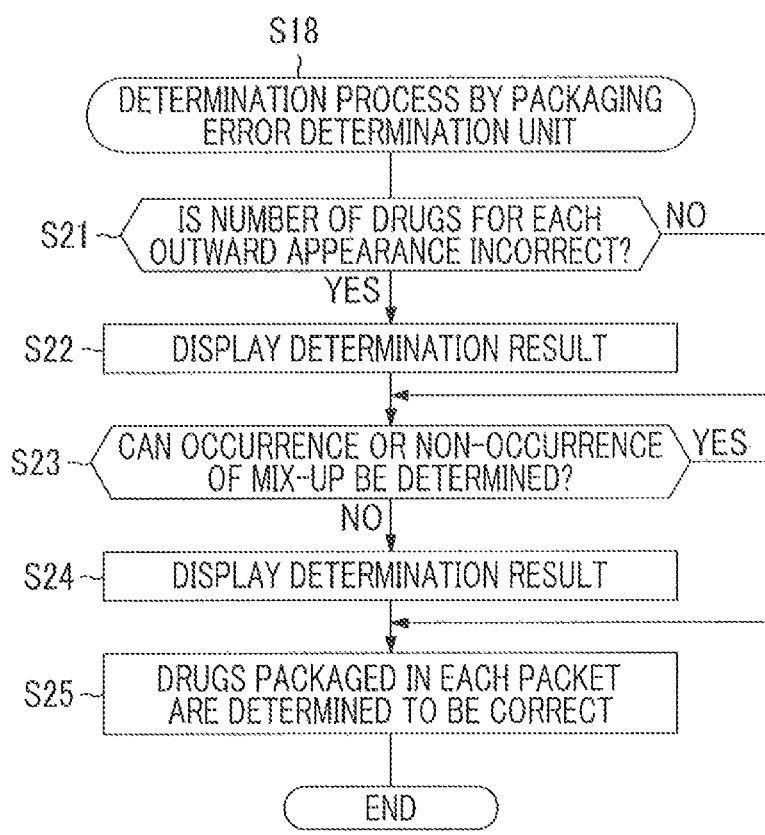
FIG. 10 is a flowchart illustrating the flow of a determination process performed by a packaging error determination unit.

As illustrated in FIG. 10, when the number of drugs 25 for each outward appearance which are packaged in a packet 27 is incorrect, the packaging error determination unit 48 determines that the drugs 25 packaged in the packet 27 are incorrect and outputs the determination result J2 to the display unit 34 (YES in Step S21). Then, as illustrated in FIG. 7, warning information indicating the packet 27 in which the number of drugs 25 for each outward appearance is incorrect is displayed on the display unit 34. Therefore, it is possible to call the attention of the pharmacist who performs the dispensing inspection operation 14 (Step S22). When the number of drugs 25 for each outward appearance which are packaged in each packet 27 is correct (NO in Step S21), information indicating that the number of drugs 25 is correct may be displayed on the display unit 34.

Then, when the occurrence or non-occurrence of the mix-up of different types of drugs 25 cannot be determined, the packaging error determination unit 48 determines that the drugs 25 packaged in each packet 27 are likely to be incorrect and outputs the determination result J3 to the display unit 34 (NO in Step S23). Then, as illustrated in FIG. 8, the type of the drug 25 whose mix-up cannot be determined is displayed on the display unit 34. Therefore, it is possible to call the attention of the pharmacist who performs the dispensing inspection operation 14 (Step S24). In addition, when the occurrence or non-occurrence of the mix-up of different types of drugs 25 can be determined (YES in Step S23), information indicating that the occurrence or non-occurrence of the mix-up can be determined may be displayed on the display unit 34.

When the number of drugs 25 for each outward appearance which are packaged in each packet 27 is correct and the occurrence or non-occurrence of the mix-up of the drugs 25 can be determined, the packaging error determination unit 48 determines that the drugs 25 packaged in each packet 27 are correct (Step S25). In this case, information indicating that the drugs 25 packaged in each packet 27 are correct may be displayed on the display unit 34. In this way, the inspection process of the packaged drug inspection device 20 is completed.

Returning to FIG. 9, the automatic packaging operation 13 is performed at the same time as the inspection process of the packaged drug inspection device 20 or after the inspection process. Then, the dispensing inspection operation 14 and the medication counseling and prescribing operation 15 are sequentially performed (Step S27). Then, whenever the pharmacist receives a new prescription, the process in each step is repeatedly performed (Step S28).

<Operation and Effect of Packaged Drug Inspection Device>

The packaged drug inspection device 20 according to the invention can determine whether the inserted drug type is correct, whether the number of drugs 25 for each outward appearance which are packaged in each packet 27 is correct, and whether the occurrence or non-occurrence of the mix-up of different types of drugs 25 can be determined to accurately determine whether the drugs 25 packaged in each packet 27 are correct. Therefore, it is possible to appropriately simplify the inspection by the pharmacist on the drug which has been determined to be correct in the dispensing inspection operation 14. Therefore, it is not necessary to inspect all of the packaged drugs 25 with the same carefulness. In addition, the packaged drug inspection device 20 can be basically implemented by various arithmetic devices (for example, computers) having arithmetic processing functions and the first and second cameras 31 and 32. Therefore, it is possible to form the packaged drug inspection device 20 at a low cost. As a result, it is possible to reduce the burden of the pharmacist to dispensing inspection at a low cost.

In the first embodiment, the second camera 32 captures the image of the drugs 25 corresponding to each dose before packaging. However, for example, the second camera 32a illustrated in FIG. 1 may be used to capture the image of the drugs 25 packaged in each packet. The image data of the drugs 25 captured by the second camera 32a is output to the number-by-appearance counting unit 45. In this way, the number-by-appearance counting unit 45 obtains the measurement information 55 similarly to the case in which the image is captured by the second camera 32.

Packaged Drug Inspection Device According to Second Embodiment

Figure 11:
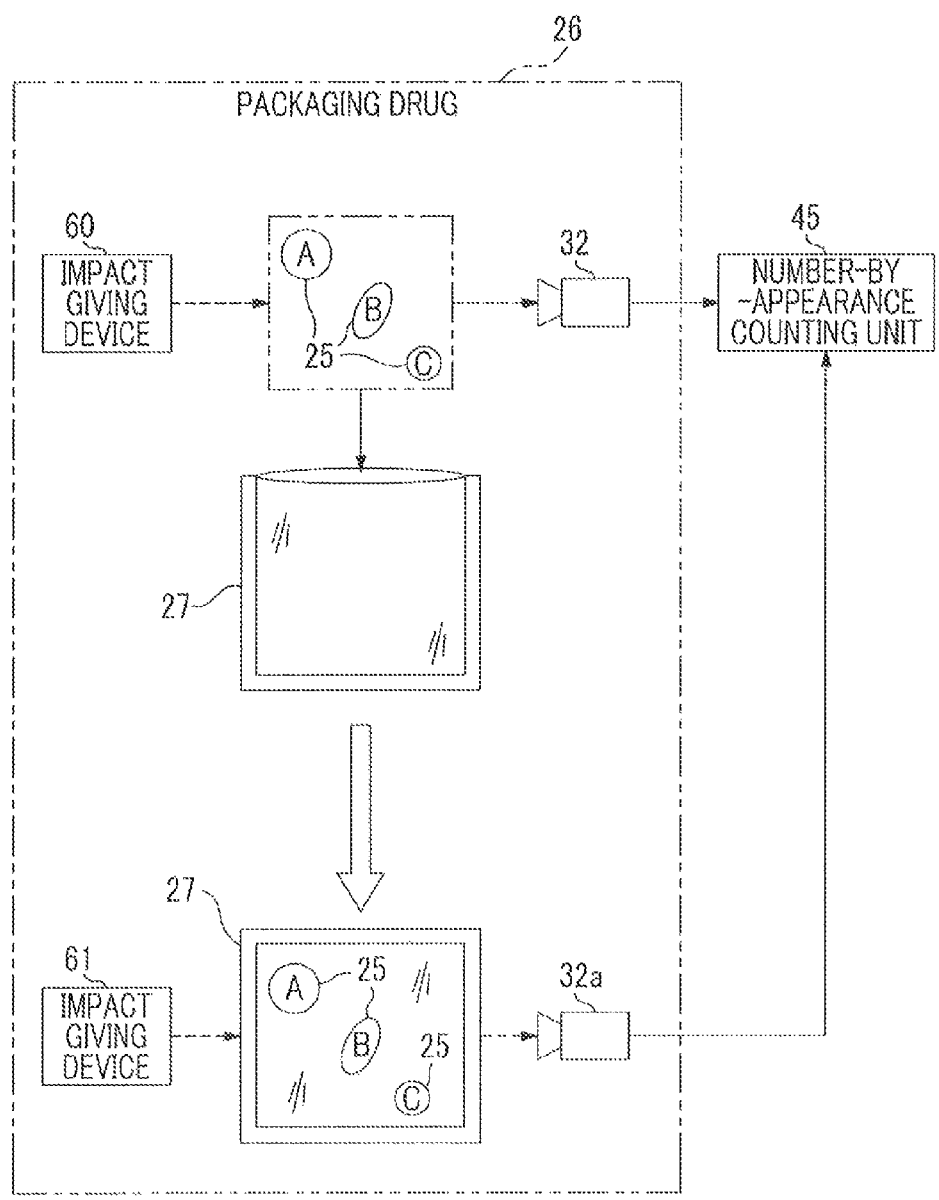
FIG. 11 is a diagram schematically illustrating a packaged drug inspection device according to a second embodiment which captures the image of drugs before and after packaging.

Next, a packaged drug inspection device according to a second embodiment of the invention will be described with reference to FIG. 11. In the packaged drug inspection device 20 according to the first embodiment, the second camera 32 captures the image of the drugs 25 corresponding to each dose before packaging or the second camera 32a captures the image of the drugs 25 packaged in each packet. However, in the second embodiment, the second camera 32 captures the image of the drugs 25 corresponding to each dose before packaging or the second camera 32a captures the image of the drugs 25 packaged in each packet. In addition, the packaged drug inspection device according to the second embodiment basically has the same structure as the packaged drug inspection device 20 according to the first embodiment except that the image of the drugs 25 is captured before and after packaging.

A number-by-appearance counting unit 45 according to the second embodiment analyzes the image data of the drugs 25 corresponding to each dose, which is input from the second camera 32 and the second camera 32a, to count the numbers of drugs for each outer appearance before and after packaging. Then, when the counting results of the numbers of drugs for each outer appearance before and after packaging are equal to each other, the number-by-appearance counting unit 45 outputs the counting results as measurement information 55 to a number-by-appearance error determination unit 46.

On the other hand, when the counting results of the numbers of drugs for each outer appearance before and after packaging are different from each other, the number-by-appearance counting unit 45 selects, for example, the larger of the counting results as a correct counting result. This is because the drug 25 which is not counted due to, for example, the overlap between the drugs 25 is likely to be present in the smaller of the counting results. In addition, in this case, a warning indicating that the counting results of the numbers of drugs for each outer appearance before and after packaging are different from each other may be displayed on the display unit 34.

As such, in the packaged drug inspection device according to the second embodiment, since the image of the drugs 25 is captured before and after packaging, accurate measurement information 55 is obtained.

The packaged drug inspection device according to the second embodiment includes impact giving devices (impact giving units) 60 and 61 which give various impacts, such as vibration or air blowing, to the drug 25 (before packaging) before the image is captured by the second camera 32 or the second camera 32a. This structure prevents the second camera 32 and the second camera 32a from capturing images while the drugs 25 overlap each other or rise vertically. Therefore, accurate measurement information 55 is obtained. In addition, impact giving devices 60 and 61 may be provided in the packaged drug inspection device 20 according to the first embodiment.

Figure 12:
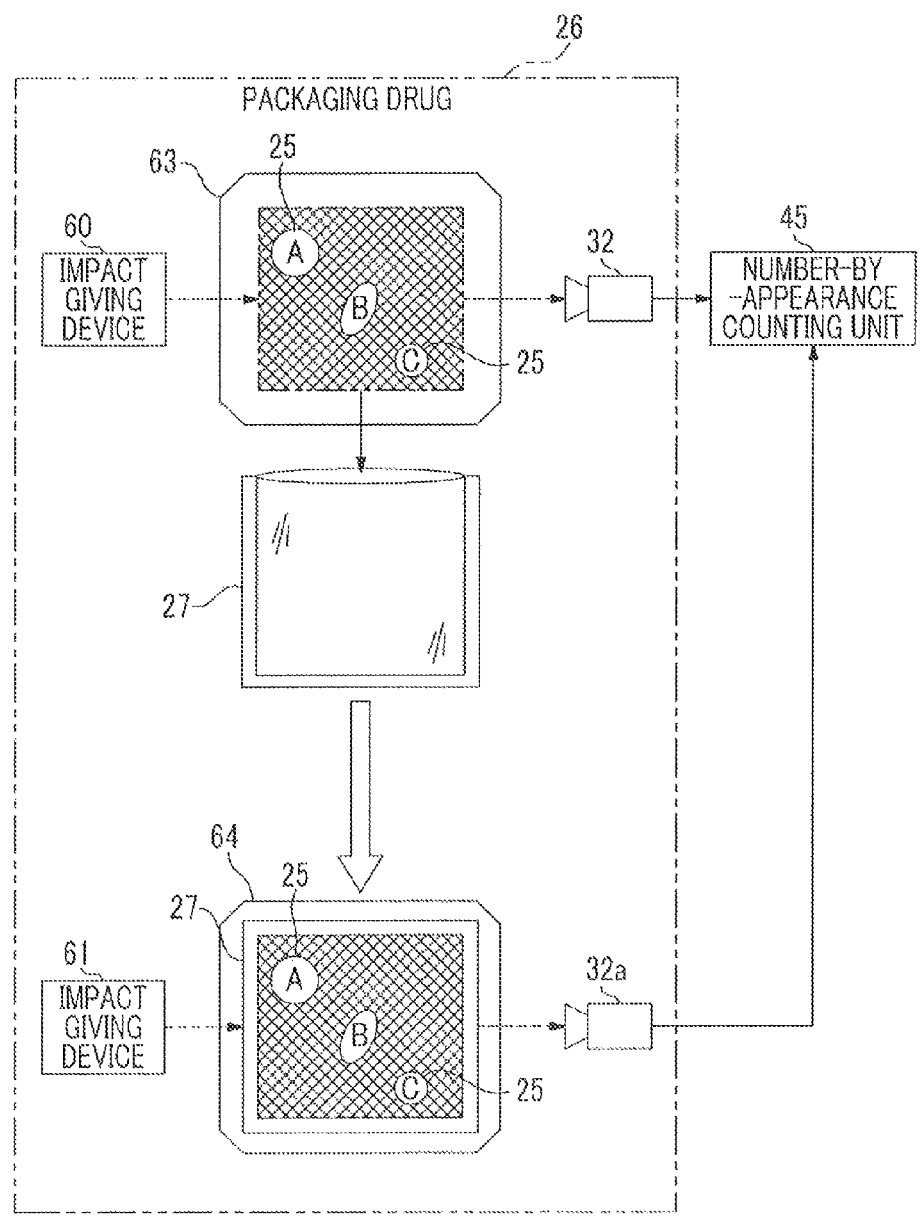
FIG. 12 is a diagram schematically illustrating another example of the packaged drug inspection device according to the second embodiment which captures the image of drugs on a black background.

As illustrated in FIG. 12, in the packaged drug inspection device according to the second embodiment, when the second camera 32 and the second camera 32a capture images, the drugs 25 may be set on black stages 63 and 64 and the image of the drugs 25 may be captured on a black background (cross-hatched in FIG. 12). The capture of the image on the black background makes it easy for the number-by-appearance counting unit 45 to extract the contour of the drug 25 from the image. In particular, even when, for example, characters are recorded on the packet 27, the capture of the image of the packaged drugs 25 on the black background prevents the characters from being included in the captured image. Therefore, accurate measurement information 55 is obtained. In addition, the image of the drugs 25 may be captured on the black background in the packaged drug inspection device 20 according to the first embodiment.

Packaged Drug Inspection Device According to Third Embodiment

Figure 13:
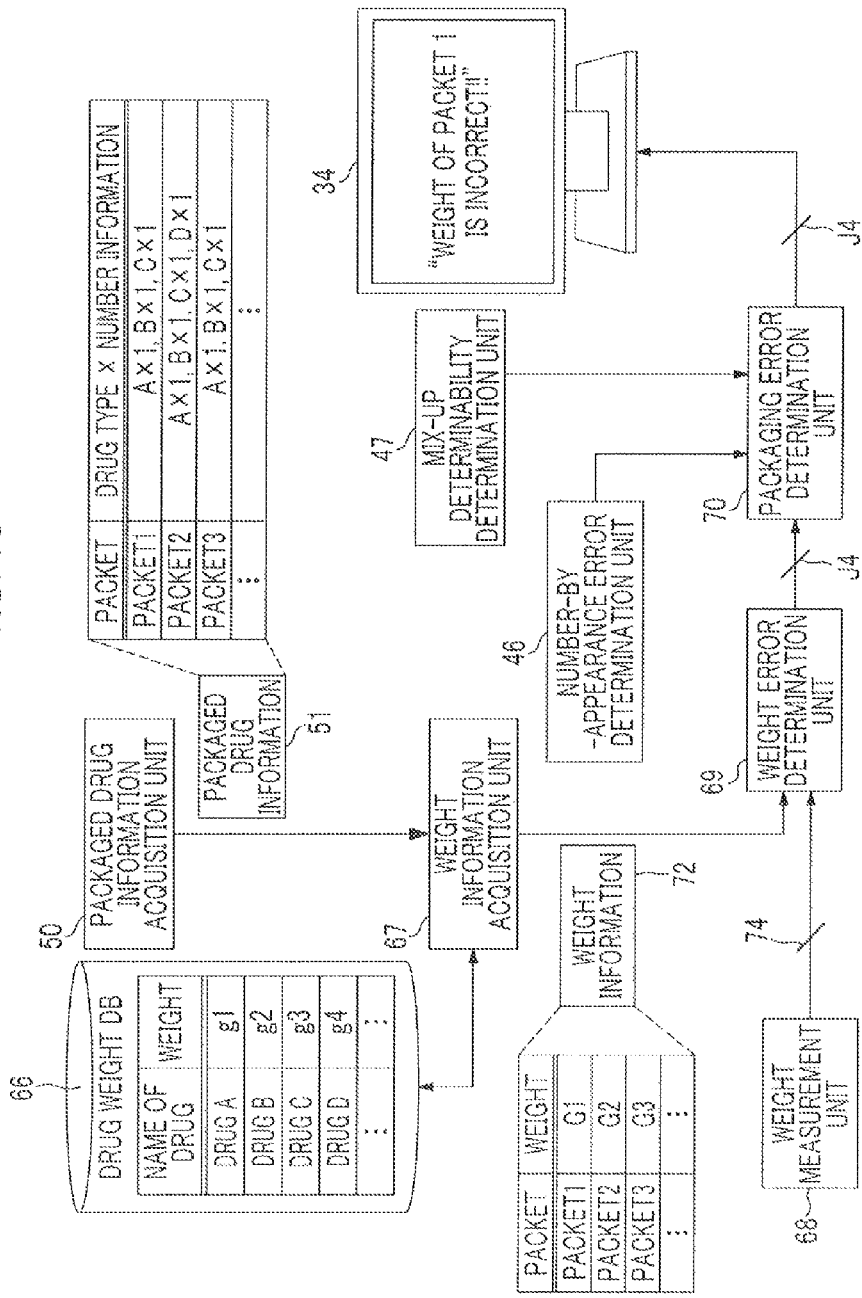
FIG. 13 is a diagram schematically illustrating a packaged drug inspection device according to a third embodiment which determines whether the weight of drugs corresponding to each dose is correct.

Next, a packaged drug inspection device according to a third embodiment of the invention will be described with reference to FIG. 13. The packaging error determination unit 48 according to the first embodiment determines whether the drugs 25 packaged in each packet 27 are correct, on the basis of the determination result J2 of the number-by-appearance error determination unit 46 and the determination result J3 of the mix-up determinability determination unit 47. In contrast, the packaged drug inspection device according to the third embodiment determines whether the drugs 25 packaged in each packet 27 are correct, on the basis of the weight of the drugs 25 which are packaged in one packet 27, in addition to the determination results J2 and J3.

The packaged drug inspection device according to the third embodiment basically has the same structure as the packaged drug inspection device 20 according to the first embodiment except that it includes a drug weight database (hereinafter, simply referred to as a drug weight DB) 66, a weight information acquisition unit 67, a weight measurement unit 68, and a weight error determination unit 69, and a packaging error determination unit 70. Therefore, components having the same functions and structures as those in the first embodiment are denoted by the same reference numerals and the description thereof will not be repeated.

The type of the drug 25 and the weight (g1, g2, ...) of the drug 25 are stored in advance in the drug weight DB 66 so as to be associated with each other. In this embodiment, the drug weight DB 66 is separately provided. However, the weight of the drug 25 may be stored in the drug information DB 41 and the drug appearance DB 43.

The weight information acquisition unit 67 is connected to the packaged drug information acquisition unit 50, the drug weight DB 66, and the weight error determination unit 69. The weight information acquisition unit 67 acquires weight information 72 indicating the weight (G1, G2, ...) of a packet of the drugs 25 which are packaged in each packet 27, with reference to the drug weight DB 66, on the basis of the packaged drug information 51 input from the packaged drug information acquisition unit 50. For example, when the packaged drug information 51 corresponding to the packet 27, which is "packet 1", is "A×1, B×1, C×1", the weight information acquisition unit 67 determines weight information 72 of "packet 1" to be G1 (=g1+g2+g3), with reference to the weight corresponding to drugs A, B, and C in the drug weight DB 66. Similarly, the weight information acquisition unit 67 determines weight information 72 corresponding to the packets 27 which are "packet 2, packet 3, ...". Then, the weight information acquisition unit 67 outputs the weight information 72 of each packet 27 to the weight error determination unit 69.

In this embodiment, the weight information acquisition unit 67 acquires the weight information 72 on the basis of the packaged drug information 51 acquired from the packaged drug information acquisition unit 50. However, the weight information acquisition unit 67 may have the function of the packaged drug information acquisition unit 50. That is, the packaged drug information acquisition unit 50 may not be provided and the weight information acquisition unit 67 may acquire the weight information 72, with reference to the drug weight DB 66, on the basis of the dispensing information 22 and the drug type information 37 acquired from, for example, the inserted drug type error determination unit 42. In this case, the weight information acquisition unit 67 can acquire the weight information 72 on the basis of at least the dispensing information 22 and the drug type information 37.

The weight measurement unit 68 measures the weight of the drugs 25 corresponding to each dose before packaging and outputs weight measurement data 74, which is the measurement result, to the weight error determination unit 69. In addition, the weight measurement unit 68 is not particularly limited as long as it can measure the weight of the drugs 25 with predetermined accuracy. The weight measurement unit 68 may be provided integrally with the packaging machine 26.

The weight error determination unit 69 checks the weight information 72 input from the weight information acquisition unit 67 and the weight measurement data 74 input from the weight measurement unit 68. Then, the weight error determination unit 69 determines whether the weight of the drugs 25 which are packaged in one packet 27 is correct, on the basis of whether the weight measurement data 74 of each packet is identical to the weight information 72 of each packet. A determination result J4 is output from the weight error determination unit 69 to the packaging error determination unit 70. At that time, when the weight of the drug 25 inserted into one packet 27 is incorrect, the weight error determination unit 69 outputs the determination result J4 including information indicating the packet 27 to the packaging error determination unit 70.

The packaging error determination unit 70 determines whether the drugs 25 packaged in each packet 27 are correct, on the basis of the determination result J2 of the number-by-appearance error determination unit 46, the determination result J3 of the mix-up determinability determination unit 47, and the determination result J4 of the weight error determination unit 69. Specifically, the packaging error determination unit 70 determines that the drugs 25 packaged in each packet 27 are correct when the number of drugs 25 for each outward appearance which are packaged in each packet 27 are correct, the occurrence or non-occurrence of the mix-up of different types of drugs 25 can be determined, and the weight of the drugs 25 which are packaged in one packet 27 is correct.

On the other hand, when the weight of the drugs 25 which are packaged in one packet 27 is incorrect, the packaging error determination unit 70 determines that the drugs 25 packaged in the packet 27 are incorrect. Then, the packaging error determination unit 70 outputs the determination result J4 indicating the packet 27 to the display unit 34. Then, information indicating the packet 27 (for example, packet 1 illustrated in FIG. 6B) whose weight is incorrect is displayed on the display unit 34.

When the number of drugs 25 for each outward appearance which are packaged in each packet 27 is not correct or when the occurrence or non-occurrence of the mix-up of different types of drugs 25 cannot be determined, the packaging error determination unit 70 performs the same process as the packaging error determination unit 48 according to the first embodiment.

The packaged drug inspection device according to the third embodiment of the invention determines whether the drugs 25 packaged in the packet 27 are correct, on the basis of the determination result J4 of the weight error determination unit 69, in addition to the determination results J2 and J3 of the number-by-appearance error determination unit 46 and the mix-up determinability determination unit 47. Therefore, the accuracy of determination can be higher than that in the first embodiment.

Other Embodiments

The mix-up determinability determination unit 47 according to each of the above-described embodiments compares the outward appearances of different types of drugs 25 (whether the outward appearances satisfy the first to third conditions), on the basis of the mix-up possibility information 58, to determine whether the occurrence or non-occurrence of the mix-up of different types of drugs 25 can be determined. In contrast, a combination of the drugs 25 whose mix-up cannot be determined may be calculated in advance and it may be determined whether the occurrence or non-occurrence of the mix-up of different types of drugs 25 can be determined, on the basis of the combination.

Figure 14:
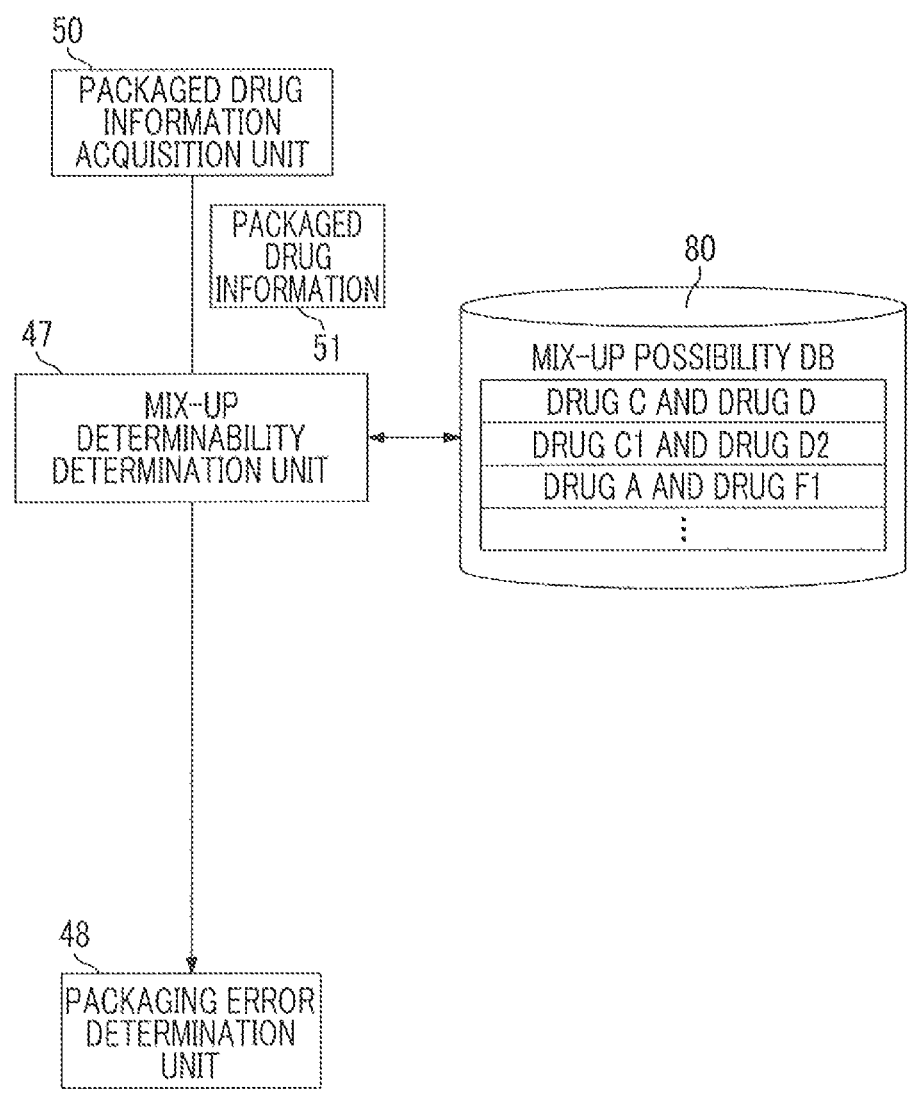
FIG. 14 is a diagram illustrating another determination process performed by the mix-up determinability determination unit.

For example, as illustrated in FIG. 14, a combination of the drugs 25 whose mix-up cannot be determined is stored in an error possibility database (hereinafter, simply referred to as an error possibility DB) 80 in advance.

The mix-up determinability determination unit 47 determines whether the combination of the drugs 25 stored in the error possibility DB 80 is included in different types of drugs 25 which are packaged in different packets 27 or the same packet 27, on the basis of the packaged drug information 51, with reference to the error possibility DB 80. Then, when the combination of the drugs 25 stored in the error possibility DB 80 is included in different types of drugs 25, the mix-up determinability determination unit 47 determines that the occurrence or non-occurrence of the mix-up of different types of drugs 25 cannot be determined.

When the combination of the drugs 25 stored in the error possibility DB 80 is not included in different types of drugs 25, the mix-up determinability determination unit 47 determines that the occurrence or non-occurrence of the mix-up of different types of drugs 25 can be determined. The subsequent processes are the same as those in the first embodiment and thus the detailed description thereof will not be repeated.

In each of the above-described embodiments, various kinds of warning information are displayed on a display surface of the display unit 34, for example, when the inserted drug type is incorrect, when the number of drugs for each outward appearance is incorrect, when the occurrence or non-occurrence of the mix-up of the drugs 25 cannot be determined, and when the weight of the drugs 25 corresponding to one packet is incorrect. However, a voice display unit which displays the warning information with a voice or various other display units may be used, instead of the display unit 34.

In each of the above-described embodiments, the packaged drug inspection device 20 used in the drug prescribing operation 10 is given as an example. However, the invention can be applied to packaged drug inspection devices which inspect the drugs 25 packaged by various packaging machines.

EXPLANATION OF REFERENCES

20: PACKAGED DRUG INSPECTION DEVICE
22: DISPENSING INFORMATION
25: DRUG
26: PACKAGING MACHINE
31: FIRST CAMERA
32: SECOND CAMERA
33: INSPECTION DEVICE BODY
34: DISPLAY UNIT
37: DRUG TYPE INFORMATION
40: INSERTED DRUG TYPE INFORMATION ACQUISITION UNIT
41: DRUG INFORMATION DATABASE
42: INSERTED DRUG TYPE ERROR DETERMINATION UNIT
43: DRUG APPEARANCE DATABASE
44: NUMBER-BY-APPEARANCE INFORMATION ACQUISITION UNIT
45: NUMBER-BY-APPEARANCE COUNTING UNIT
46: NUMBER-BY-APPEARANCE ERROR DETERMINATION UNIT
47: MIX-UP DETERMINABILITY DETERMINATION UNIT
48: PACKAGING ERROR DETERMINATION UNIT

What is claimed is:

1. A packaged drug inspection device comprising:
one or more processors configured to perform steps of:
acquiring prescription information of drugs packaged in a packet according to at least one of patient age and dosing information;
acquiring drug type information of the drugs inserted into a packaging machine which packages the drugs in the packet;
determining whether the type of the drug inserted into the packaging machine is correct as an inserted drug type error determination, on the basis of at least the prescription information and the drug type information;
acquiring number-by-appearance information indicating a number of drugs for each outward appearance, which correspond to each dose and are packaged in each packet, on the basis of at least the prescription information and the drug type information;
capturing an image of the drugs corresponding to each dose;
counting the number of drugs for each outward appearance which correspond to each dose to obtain a number-by-appearance count, on the basis of the image of the drugs captured by the image capturing step;
determining a number-by-appearance error, which is whether the number of drugs for each outward appearance which correspond to each dose is correct, on the basis of the number-by-appearance information and the counting result of the number-by-appearance count;
determining a possibility of error occurrence, which is whether the occurrence or non-occurrence of a mix-up in which a different type of drug is put in the packet, instead of the drug to be put in the packet, can be determined, on the basis of at least the prescription information and the drug type information;
determining whether the drugs packaged in each packet are correct, on the basis of the determination result of the number-by-appearance error determination step and the determination result of the possibility of error occurrence determination step, and determines that the drugs are correct when the number-by-appearance error determination step determines that the number of drugs is correct and the possibility of error occurrence determination step determines that the possibility of error occurrence can be determined; and
a drug appearance database that stores the type of the drug and drug appearance information indicating the outward appearance of the drug so as to be associated with each other,
wherein the number-by-appearance information acquisition step acquires the number-by-appearance information, on the basis of the prescription information and the drug type information, with reference to the drug appearance database, and
wherein the possibility of error occurrence determination step acquires the drug appearance information of the drug from the drug appearance database and determines that the possibility of error cannot be determined when different types of drugs having the same or similar outward appearance are included in the drugs to be packaged on the basis of the drug appearance information, the prescription information, and the drug type information.

2. The packaged drug inspection device according to claim 1, further comprising:
a drug information database that stores the type of the drug and the drug type information recorded on a package of the drug so as to be associated with each other,
wherein the acquiring drug type information step comprises acquiring the drug type information from the package, and
wherein the determining whether the drug type is correct is performed on the basis of the prescription information and the drug type information, with reference to the drug information database.

3. The packaged drug inspection device according to claim 2, wherein the drug type information acquiring step acquires at least one of characters, a barcode, and electronic identification information recorded on the package as the drug type information.

4. The packaged drug inspection device according to claim 2,
wherein the drug information database stores information indicating a correspondence relationship between an original drug and a generic drug, and
when the drug corresponding to the drug type information has the same effective ingredients as the drug designated by the prescription information, the inserted drug type error determining step determines that the drug type is correct.

5. The packaged drug inspection device according to claim 1, further comprising:
a first display that displays the drug type when the inserted drug type error determining step determines that the drug type is incorrect.

6. The packaged drug inspection device according to claim 1, further comprising:
a second display that, when the possibility of error occurrence determination step determines that the occurrence or non-occurrence of the mix-up cannot be determined, displays the determination result that possibility of error occurrence cannot be determined.

7. The packaged drug inspection device according to claim 6,
wherein the second display displays the drug whose possibility of error occurrence cannot be determined.

8. The packaged drug inspection device according to claim 1,
wherein the drug appearance information includes information indicating at least one of a size, type, and color of the drug, and
wherein the number-by-appearance count comprises the number of drugs for each outward appearance for each item corresponding to the drug appearance information.

9. The packaged drug inspection device according to claim 1, further comprising:
a third display that, when the determining whether the number of drugs for each outward appearance is incorrect, displays the determination result of the number-by-appearance error determining step.

10. The packaged drug inspection device according to claim 1,
wherein the capturing the image of the drugs is performed before the drugs are packaged in each packet and/or after the drugs are packaged in each packet.

11. The packaged drug inspection device according to claim 1,
wherein capturing the image of the drugs is performed on a black background.

12. The packaged drug inspection device according to claim 1,
wherein, when capturing the image of the drugs after packaging, the image capturing step captures the image of the inside of the packet from a transparent side of the packet.

13. The packaged drug inspection device according to claim 1, the one or more processors configured to further perform a step of:
providing an physical adjustment to the drugs before the step of capturing the image of the drugs.

14. The packaged drug inspection device according to claim 1, the one or more processors configured to further perform steps of:

measuring the weight of the drugs corresponding to each dose;
acquiring weight information indicating the weight of the drugs corresponding to each dose, on the basis of at least the prescription information and the drug type information; and
determining whether the weight of the drugs corresponding to each dose is correct as a weight error determination on the basis of the weight information and the measurement result of measuring the weight of the drugs corresponding to each does,
wherein the step of determining whether the drugs packaged in each packet are correct is performed on the basis of the weight error determination.

15. A packaged drug inspection method comprising:
a prescription information acquisition step of acquiring prescription information of drugs packaged in a packet according to at least one of patient age and dosing information;
an inserted drug type information acquisition step of acquiring drug type information of the drugs inserted into a packaging machine which packages the drugs in the packet;
an inserted drug type error determination step of determining whether the type of the drug inserted into the packaging machine is correct, on the basis of at least the prescription information and the drug type information;
a number-by-appearance information acquisition step of acquiring number-by-appearance information indicating a number of drugs for each outward appearance, which correspond to each dose and are packaged in each packet, on the basis of at least the prescription information and the drug type information;
an imaging step of capturing an image of the drugs corresponding to each dose;
a number-by-appearance counting step of counting the number of drugs for each outward appearance, which correspond to each dose, on the basis of the image of the drugs captured in the imaging step;
a number-by-appearance error determination step of determining whether the number of drugs for each outward appearance, which correspond to each dose, is correct, on the basis of the number-by-appearance information and the counting result in the number-by-appearance counting step;
a possibility of error occurrence determining step of determining whether the occurrence or non-occurrence of a mix-up in which a different type of drug is put in the packet, instead of the drug to be put in the packet, can be determined, on the basis of at least the prescription information and the drug type information; and
a packaging error determination step of determining whether the drugs packaged in each packet are correct, on the basis of the determination result in the number-by-appearance error determination step and the determination result in the possibility of error occurrence determining step, and of determining that the drugs are correct when it is determined in the number-by-appearance error determination step that the number of drugs is correct and it is determined in the possibility of error occurrence determining step that the occurrence or non-occurrence of the mix-up can be determined;
acquiring information from a drug appearance database that stores the type of the drug and drug appearance information indicating the outward appearance of the drug so as to be associated with each other, wherein the number-by-appearance information acquisition step acquires the number-by-appearance information, on the basis of the prescription information and the drug type information, with reference to the drug appearance database, and wherein the possibility of error occurrence determining step acquires the drug appearance information of the drug from the drug appearance database and determines that the possibility of error cannot be determined when different types of drugs having the same or similar outward appearance are included in the drugs to be packaged on the basis of the drug appearance information, the prescription information, and the drug type information.

16. The packaged drug inspection method according to claim 15, wherein in the inserted drug type information acquisition step, the drug type information is acquired from a package with reference a drug information database in which the type of the drug and the drug type information recorded on the package of the drug are stored so as to be associated with each other, and in the inserted drug type error determination step, whether the drug type is correct is determined on the basis of the prescription information and the drug type information with reference to the drug information database.

17. The packaged drug inspection method according to claim 16, wherein in the inserted drug type information acquisition step, at least one of characters, a barcode, and electronic identification information recorded on the package is acquired as the drug type information.

18. The packaged drug inspection method according to claim 16, wherein the drug information database stores information indicating a correspondence relationship between an original drug and a generic drug, and in the inserted drug type error determination step, when the drug corresponding to the drug type information has the same effective ingredients as the drug designated by the prescription information, the drug type is determined as correct.

* * * * *